United States Patent
Verri et al.

(10) Patent No.: US 10,376,627 B2
(45) Date of Patent: Aug. 13, 2019

(54) FLEXIBLE BIOLOGICAL FLUID FILTERS

(71) Applicant: Fenwal, Inc., Lake Zurich, IL (US)

(72) Inventors: Paolo Verri, Carpi (IT); Daniel Lynn, Spring Grove, IL (US); Scott Day, Buffalo Grove, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 15/127,042

(22) PCT Filed: Jun. 6, 2014

(86) PCT No.: PCT/US2014/041210
§ 371 (c)(1),
(2) Date: Sep. 19, 2016

(87) PCT Pub. No.: WO2015/147896
PCT Pub. Date: Oct. 1, 2015

(65) Prior Publication Data
US 2017/0136167 A1    May 18, 2017

Related U.S. Application Data

(63) Continuation-in-part of application No. 14/222,961, filed on Mar. 24, 2014, now Pat. No. 9,796,166.

(51) Int. Cl.
*A61M 1/34* (2006.01)
*A61M 1/36* (2006.01)
*A61M 1/02* (2006.01)

(52) U.S. Cl.
CPC ........ *A61M 1/3636* (2014.02); *A61M 1/0281* (2013.01); *A61M 2202/0439* (2013.01); *A61M 2205/3331* (2013.01); *Y10T 156/10* (2015.01)

(58) Field of Classification Search
CPC . B32B 37/144; B32B 37/18; B32B 2307/726; B32B 2535/00; B32B 2327/06;
(Continued)

(56) References Cited

U.S. PATENT DOCUMENTS

| 2,702,034 A | 2/1955 | Walter |
| 2,781,064 A | 2/1957 | Dawkins |

(Continued)

FOREIGN PATENT DOCUMENTS

| BE | 1005193 A3 | 5/1993 |
| DE | 82 20 399 U1 | 10/1982 |

(Continued)

OTHER PUBLICATIONS

International Search Report and Written Opinion dated Nov. 26, 2014 for International Application No. PCT/US2014/041213.
(Continued)

*Primary Examiner* — Madeline Gonzalez
(74) *Attorney, Agent, or Firm* — Cook Alex Ltd.

(57) ABSTRACT

Filter assemblies are processing biological fluid, such as blood or a blood component containing leukocytes. The filter assemblies include a flexible housing with first and second walls. A filtration medium and a support member are at least partially positioned between the walls of the housing, with a seal joining the walls of the housing, the filtration medium, and the support member. The filter assemblies may further include a pre-filter and/or a post-filter positioned between the walls of the housing. If provided, the pre- and post-filter may be positioned on opposite walls of the filtration medium, with the post-filter being a mesh positioned between the filtration medium and one of the walls of the housing or within an opening defined by the support member. A seal of the filter assembly may pass through the filtration medium, with the filtration medium being substantially omitted in a section of the seal.

23 Claims, 7 Drawing Sheets

(58) Field of Classification Search
CPC ........ B32B 2307/412; B32B 2307/546; A61M 1/3636; A61M 2202/0439; A61M 1/34; Y10T 156/10
USPC ................. 210/450, 645, 782, 94, 499, 335, 210/488–490
See application file for complete search history.

(56) References Cited

U.S. PATENT DOCUMENTS

| | | |
|---|---|---|
| 3,523,408 A | 8/1970 | Rosenberg |
| 3,631,654 A | 1/1972 | Riely |
| 3,650,093 A | 3/1972 | Rosenberg |
| 3,705,100 A | 12/1972 | Blatt et al. |
| 3,752,385 A | 8/1973 | Woodgate |
| 3,765,536 A | 10/1973 | Rosenberg |
| 3,765,537 A | 10/1973 | Rosenberg |
| 3,803,810 A | 4/1974 | Rosenberg |
| 3,892,236 A | 7/1975 | Djerassi |
| 3,905,905 A | 9/1975 | O'Leary et al. |
| 3,935,110 A | 1/1976 | Schmid et al. |
| 4,009,714 A | 3/1977 | Hammer |
| 4,009,715 A | 3/1977 | Forberg et al. |
| 4,035,304 A | 7/1977 | Watanabe |
| 4,066,556 A * | 1/1978 | Vaillancourt ......... A61M 5/165 210/448 |
| 4,092,246 A | 5/1978 | Kummer |
| 4,132,650 A | 1/1979 | Kirsch et al. |
| 4,136,796 A | 1/1979 | Dubois et al. |
| 4,190,426 A | 2/1980 | Ruschke |
| 4,223,695 A | 9/1980 | Muetterties |
| 4,246,107 A | 1/1981 | Takenaka et al. |
| 4,276,170 A | 6/1981 | Vaillancourt |
| 4,283,289 A | 8/1981 | Meyst et al. |
| 4,284,209 A | 8/1981 | Barbour, Jr. |
| 4,294,594 A | 10/1981 | Sloane, Jr. et al. |
| 4,330,410 A | 5/1982 | Takenaka et al. |
| 4,340,049 A | 6/1982 | Munsch |
| 4,360,435 A | 11/1982 | Bellamy et al. |
| 4,374,731 A | 2/1983 | Brown et al. |
| 4,401,567 A | 8/1983 | Shindo et al. |
| 4,416,777 A | 11/1983 | Kuroda et al. |
| 4,460,366 A | 7/1984 | Shinno |
| 4,479,762 A | 10/1984 | Bilstad et al. |
| 4,525,182 A | 6/1985 | Rising et al. |
| 4,596,657 A | 6/1986 | Wisdom |
| 4,635,467 A | 1/1987 | Hoffa et al. |
| 4,679,693 A | 7/1987 | Forman |
| 4,701,267 A | 10/1987 | Watanabe et al. |
| 4,753,739 A | 6/1988 | Noble |
| 4,767,541 A | 8/1988 | Wisdom |
| 4,810,378 A | 3/1989 | Carmen et al. |
| 4,838,872 A | 6/1989 | Sherlock |
| 4,855,063 A | 8/1989 | Carmen et al. |
| 4,880,548 A | 11/1989 | Pall et al. |
| 4,892,668 A | 1/1990 | Harmony et al. |
| 4,896,772 A | 1/1990 | Walter et al. |
| 4,898,573 A | 2/1990 | Takenaka et al. |
| 4,906,260 A | 3/1990 | Emheiser et al. |
| 4,915,848 A | 4/1990 | Carmen et al. |
| 4,919,823 A | 4/1990 | Wisdom |
| 4,923,620 A | 5/1990 | Pall |
| 4,925,572 A | 5/1990 | Pall |
| 4,936,993 A | 6/1990 | Nomura |
| 4,936,998 A | 6/1990 | Nishimura et al. |
| 4,963,260 A | 10/1990 | Naoi et al. |
| 4,976,861 A | 12/1990 | Pall |
| 4,985,153 A | 1/1991 | Kuroda et al. |
| 4,997,577 A | 3/1991 | Stewart |
| 5,015,369 A | 3/1991 | Romine et al. |
| 5,071,553 A | 12/1991 | Newlin |
| 5,071,570 A | 12/1991 | Shiraki et al. |
| 5,092,996 A | 3/1992 | Spielberg |
| 5,100,564 A | 3/1992 | Pall et al. |
| 5,104,788 A | 4/1992 | Carmen et al. |
| 5,128,048 A | 7/1992 | Stewart et al. |
| 5,141,645 A | 8/1992 | Shiraki et al. |
| 5,152,905 A | 10/1992 | Pall et al. |
| 5,154,716 A | 10/1992 | Bauman et al. |
| 5,164,087 A | 11/1992 | Naoi et al. |
| 5,180,504 A | 1/1993 | Johnson et al. |
| 5,182,017 A | 1/1993 | Ippendorf |
| 5,234,593 A | 8/1993 | Kuroki et al. |
| 5,236,716 A | 8/1993 | Carmen et al. |
| 5,252,222 A | 10/1993 | Matkovich et al. |
| 5,254,248 A | 10/1993 | Nakamura |
| 5,258,127 A | 11/1993 | Gsell et al. |
| 5,269,946 A | 12/1993 | Goldhaber et al. |
| 5,286,449 A | 2/1994 | Kuroda et al. |
| 5,298,165 A | 3/1994 | Oka et al. |
| 5,302,299 A | 4/1994 | Pascale et al. |
| 5,316,674 A | 5/1994 | Pall et al. |
| 5,316,681 A | 5/1994 | Serres |
| 5,330,462 A | 7/1994 | Nakamura |
| 5,348,646 A | 9/1994 | Costello, Jr. et al. |
| 5,350,513 A | 9/1994 | Markowitz |
| 5,360,545 A | 11/1994 | Pall et al. |
| 5,362,406 A | 11/1994 | Gsell et al. |
| 5,364,526 A | 11/1994 | Matkovich et al. |
| 5,368,725 A | 11/1994 | Bredeweg et al. |
| 5,386,734 A | 2/1995 | Pusineill |
| 5,387,187 A | 2/1995 | Fell et al. |
| 5,393,422 A | 2/1995 | Pummell |
| 5,399,268 A | 3/1995 | Pall et al. |
| 5,403,272 A | 4/1995 | Deniega et al. |
| 5,403,304 A | 4/1995 | Ishida |
| 5,405,343 A | 4/1995 | Mohr |
| 5,407,581 A | 4/1995 | Onodera et al. |
| 5,445,629 A | 8/1995 | Debrauwere et al. |
| 5,445,736 A | 8/1995 | Pall et al. |
| 5,454,946 A | 10/1995 | Heagle et al. |
| 5,456,835 A | 10/1995 | Castino et al. |
| 5,456,845 A | 10/1995 | Nishimura et al. |
| 5,472,605 A | 12/1995 | Zuk, Jr. |
| 5,476,587 A | 12/1995 | Kuroki et al. |
| 5,476,797 A | 12/1995 | Matsunaga |
| 5,478,470 A | 12/1995 | Fukuda et al. |
| 5,498,336 A | 3/1996 | Katsurada et al. |
| 5,501,795 A | 3/1996 | Pall et al. |
| 5,507,904 A | 4/1996 | Fisher et al. |
| 5,527,472 A | 6/1996 | Bellotti et al. |
| 5,536,413 A | 7/1996 | Bormann et al. |
| 5,540,841 A | 7/1996 | Gsell et al. |
| 5,543,060 A | 8/1996 | Pall et al. |
| 5,543,062 A | 8/1996 | Nishimura |
| 5,547,576 A | 8/1996 | Onishi et al. |
| 5,547,591 A | 8/1996 | Hagihara et al. |
| 5,549,834 A | 8/1996 | Brown |
| 5,580,465 A | 12/1996 | Pall et al. |
| 5,587,070 A | 12/1996 | Pall et al. |
| 5,591,337 A * | 1/1997 | Lynn ........................ A61J 1/10 156/272.2 |
| 5,601,730 A | 2/1997 | Page et al. |
| 5,609,947 A | 3/1997 | Kamei et al. |
| 5,616,254 A | 4/1997 | Pall et al. |
| 5,632,906 A | 5/1997 | Ishida et al. |
| 5,637,271 A | 6/1997 | Suzuki et al. |
| 5,639,376 A | 6/1997 | Lee et al. |
| 5,649,903 A | 7/1997 | Deniega et al. |
| 5,660,731 A | 8/1997 | Piechocki et al. |
| 5,665,233 A | 9/1997 | Fukuda et al. |
| 5,670,060 A | 9/1997 | Matkovich et al. |
| 5,679,264 A | 10/1997 | Gsell |
| 5,690,815 A | 11/1997 | Krasnoff et al. |
| 5,695,653 A | 12/1997 | Gsell et al. |
| 5,707,520 A | 1/1998 | Kuroki et al. |
| 5,738,796 A | 4/1998 | Bormann et al. |
| 5,744,047 A | 4/1998 | Gsell et al. |
| 5,769,839 A | 6/1998 | Carmen et al. |
| 5,772,880 A | 6/1998 | Lynn et al. |
| 5,779,902 A | 7/1998 | Zuk, Jr. |
| 5,788,661 A | 8/1998 | Japuntich |
| 5,795,483 A | 8/1998 | Ung-Chhun et al. |
| 5,798,041 A | 8/1998 | Zuk |
| 5,804,280 A | 9/1998 | Pall et al. |

(56) References Cited

U.S. PATENT DOCUMENTS

| | | |
|---|---|---|
| 5,817,237 A | 10/1998 | Lee et al. |
| 5,820,755 A | 10/1998 | Kraus et al. |
| 5,836,934 A | 11/1998 | Beshel |
| 5,837,140 A | 11/1998 | Fini et al. |
| 5,885,457 A | 3/1999 | Breillatt, Jr. et al. |
| 5,895,575 A | 4/1999 | Kraus et al. |
| 5,902,490 A | 5/1999 | Zuk, Jr. |
| 5,935,436 A | 8/1999 | Lee et al. |
| 5,938,940 A | 8/1999 | Zuk, Jr. |
| 5,951,877 A | 9/1999 | Langley et al. |
| 5,954,971 A | 9/1999 | Pages et al. |
| 5,989,441 A | 11/1999 | Rashidbaigi et al. |
| 5,997,496 A | 12/1999 | Sekiguchi et al. |
| 6,010,633 A | 1/2000 | Zuk, Jr. et al. |
| 6,013,184 A | 1/2000 | Fukuda et al. |
| 6,015,500 A | 1/2000 | Zuk, Jr. |
| 6,022,306 A | 2/2000 | Dumont et al. |
| 6,030,539 A | 2/2000 | Zuk, Jr. |
| 6,032,807 A | 3/2000 | Sternberg et al. |
| 6,048,464 A | 4/2000 | Tanaka et al. |
| 6,051,136 A | 4/2000 | Mari |
| 6,053,856 A | 4/2000 | Hlavinka |
| 6,053,885 A | 4/2000 | Beshel |
| 6,074,869 A | 6/2000 | Pall et al. |
| 6,080,322 A | 6/2000 | Deniega et al. |
| 6,083,584 A | 7/2000 | Smith et al. |
| 6,086,770 A | 7/2000 | Matkovich |
| 6,102,883 A | 8/2000 | Kingsley et al. |
| 6,123,859 A | 9/2000 | Lee et al. |
| 6,129,853 A | 10/2000 | Sasayama et al. |
| 6,139,757 A | 10/2000 | Ohmura et al. |
| 6,159,375 A | 12/2000 | Lee et al. |
| 6,168,718 B1 | 1/2001 | Sutter et al. |
| 6,189,704 B1 | 2/2001 | Dennehey et al. |
| 6,197,207 B1 | 3/2001 | Chapman et al. |
| 6,200,287 B1 | 3/2001 | Keller et al. |
| 6,221,264 B1 | 4/2001 | Ishida et al. |
| 6,231,770 B1 | 5/2001 | Bormann et al. |
| 6,251,276 B1 | 6/2001 | Motomura |
| 6,251,284 B1 | 6/2001 | Bischof et al. |
| 6,267,898 B1 | 7/2001 | Fukuda et al. |
| 6,267,926 B1 | 7/2001 | Reed et al. |
| 6,274,055 B1 | 8/2001 | Zuk, Jr. |
| 6,322,604 B1 | 11/2001 | Midkiff |
| 6,325,422 B1 | 12/2001 | Verkaart et al. |
| 6,336,916 B1 | 1/2002 | Bormann et al. |
| 6,337,026 B1 | 1/2002 | Lee et al. |
| 6,348,156 B1 | 2/2002 | Vishnci et al. |
| 6,352,642 B1 | 3/2002 | Fukuda et al. |
| 6,355,174 B1 | 3/2002 | Robertson |
| 6,358,420 B2 | 3/2002 | Blickhan et al. |
| 6,428,712 B1 | 8/2002 | Castino |
| 6,488,860 B2 | 12/2002 | Mari et al. |
| 6,495,039 B1 | 12/2002 | Lee et al. |
| 6,497,685 B1 | 12/2002 | Dennehey et al. |
| 6,497,821 B1 | 12/2002 | Bellamy, Jr. et al. |
| 6,523,698 B1 | 2/2003 | Dennehey et al. |
| 6,527,957 B1 | 3/2003 | Daniega et al. |
| 6,565,782 B1 | 5/2003 | Wang et al. |
| D475,787 S | 6/2003 | Zia et al. |
| 6,592,507 B2 | 7/2003 | Jorgensen et al. |
| 6,592,613 B1 | 7/2003 | Ishida et al. |
| 6,602,812 B2 | 8/2003 | Onodera et al. |
| 6,629,613 B1 | 10/2003 | Kraus et al. |
| 6,645,388 B2 | 11/2003 | Sheikh-Ali |
| 6,660,171 B2 | 12/2003 | Zuk, Jr. |
| 6,663,586 B2 | 12/2003 | Verkaart et al. |
| 6,670,128 B2 | 12/2003 | Smith et al. |
| 6,688,935 B1 | 2/2004 | Lin |
| 6,695,805 B1 | 2/2004 | Sun et al. |
| 6,699,388 B1 | 3/2004 | Iwamoto et al. |
| 6,709,412 B2 | 3/2004 | Vandlik et al. |
| 6,723,062 B1 | 4/2004 | Westberg et al. |
| 6,723,238 B2 | 4/2004 | Romanauskas et al. |
| 6,730,054 B2 | 5/2004 | Pierce et al. |
| 6,730,055 B2 | 5/2004 | Bainbridge et al. |
| 6,740,239 B2 | 5/2004 | Hogberg et al. |
| 6,746,841 B1 | 6/2004 | Fomovskaia et al. |
| 6,767,466 B2 | 7/2004 | Kraus et al. |
| 6,773,413 B2 | 8/2004 | Keller et al. |
| 6,796,954 B2 | 9/2004 | Sawamoto et al. |
| 6,824,688 B2 | 11/2004 | Breillatt, Jr. et al. |
| 6,872,307 B2 | 3/2005 | Bischof |
| 6,875,191 B2 | 4/2005 | Smith et al. |
| 6,939,468 B2 | 9/2005 | Wang et al. |
| 6,945,411 B1 | 9/2005 | Bormann et al. |
| 6,955,700 B2 | 10/2005 | Zia et al. |
| 6,960,179 B2 | 11/2005 | Gura |
| 6,964,646 B1 | 11/2005 | Biesel |
| 6,977,044 B1 | 12/2005 | Oishi et al. |
| 6,994,790 B2 | 2/2006 | Corbin, III et al. |
| 6,997,893 B2 | 2/2006 | Mathias et al. |
| 7,011,761 B2 | 3/2006 | Muller |
| 7,025,881 B2 | 4/2006 | Helm |
| 7,041,076 B1 | 5/2006 | Westberg et al. |
| 7,052,606 B2 | 5/2006 | Gibbs et al. |
| 7,059,429 B2 | 6/2006 | Taylor et al. |
| 7,060,183 B1 | 6/2006 | Goudaliez et al. |
| 7,083,697 B2 | 8/2006 | Dao et al. |
| 7,125,493 B2 | 10/2006 | Wang et al. |
| 7,140,497 B2 | 11/2006 | Verpoort et al. |
| 7,144,496 B2 | 12/2006 | Meserol et al. |
| 7,156,240 B2 | 1/2007 | Oishi et al. |
| 7,169,547 B2 | 1/2007 | Rubinstein et al. |
| 7,182,865 B2 | 2/2007 | Latza |
| 7,186,231 B2 | 3/2007 | Takagi et al. |
| 7,217,365 B2 | 5/2007 | Fukuda et al. |
| 7,241,281 B2 | 7/2007 | Coelho et al. |
| 7,264,608 B2 | 9/2007 | Bischof et al. |
| 7,270,757 B1 | 9/2007 | Zuk, Jr. |
| 7,278,541 B2 | 10/2007 | Breillatt, Jr. et al. |
| 7,281,632 B2 | 10/2007 | Zia |
| 7,303,605 B2 | 12/2007 | Zia et al. |
| 7,332,096 B2 | 2/2008 | Blickhan |
| 7,351,344 B2 | 4/2008 | Verri et al. |
| 7,353,956 B2 | 4/2008 | Lynn et al. |
| 7,357,897 B2 | 4/2008 | Smith et al. |
| 7,361,277 B2 | 4/2008 | Bormann et al. |
| 7,374,870 B2 | 5/2008 | Herman et al. |
| 7,393,628 B2 | 7/2008 | Wagner et al. |
| 7,410,066 B2 | 8/2008 | Yamada et al. |
| 7,424,821 B1 | 9/2008 | Benjamin et al. |
| 7,438,821 B2 | 10/2008 | Yokomizo et al. |
| 7,439,013 B2 | 10/2008 | Kuno et al. |
| 7,445,124 B2 | 11/2008 | Cavallini et al. |
| 7,488,302 B1 | 2/2009 | Helm et al. |
| 7,517,333 B2 | 4/2009 | Vandlik et al. |
| 7,524,425 B2 | 4/2009 | Mari et al. |
| 7,531,098 B2 | 5/2009 | Robinson et al. |
| 7,534,348 B2 | 5/2009 | Reitz et al. |
| 7,566,315 B2 | 7/2009 | Hirabuki |
| 7,569,026 B2 | 8/2009 | Sugawara |
| 7,591,954 B2 | 9/2009 | Kimura et al. |
| 7,592,134 B2 | 9/2009 | Sato et al. |
| 7,597,677 B2 | 10/2009 | Gura et al. |
| 7,597,806 B2 | 10/2009 | Uchi et al. |
| 7,601,268 B2 | 10/2009 | Ragusa |
| 7,625,351 B2 | 12/2009 | Messier |
| 7,641,794 B2 | 1/2010 | Oka et al. |
| 7,648,452 B2 | 1/2010 | Holmes et al. |
| 7,651,474 B2 | 1/2010 | Van Waeg et al. |
| 7,655,146 B2 | 2/2010 | Ozeki et al. |
| 7,682,329 B2 | 3/2010 | Gibbs et al. |
| 7,686,779 B1 | 3/2010 | Gibbs |
| 7,686,797 B2 | 3/2010 | Zia et al. |
| 7,695,423 B2 | 4/2010 | Robinson et al. |
| 7,695,627 B2 | 4/2010 | Bosch et al. |
| 7,721,898 B2 | 5/2010 | Yagi et al. |
| 7,736,516 B2 | 6/2010 | Zambianchi et al. |
| 7,775,376 B2 | 8/2010 | Bonaguidi et al. |
| 7,789,245 B2 | 9/2010 | Westberg et al. |
| 7,789,847 B2 | 9/2010 | Gibbs et al. |
| 7,790,039 B2 | 9/2010 | Bosch et al. |
| 7,793,787 B2 | 9/2010 | Mizomoto et al. |

(56) References Cited

U.S. PATENT DOCUMENTS

| | | | |
|---|---|---|---|
| 7,819,793 B2 | 10/2010 | Lindell et al. |
| 7,820,371 B2 | 10/2010 | Onodera et al. |
| 7,854,845 B2 | 12/2010 | Zuk, Jr. |
| 7,896,830 B2 | 3/2011 | Gura et al. |
| 7,897,038 B2 | 3/2011 | Zia |
| 7,910,008 B2 | 3/2011 | Sommer et al. |
| 7,943,372 B2 | 5/2011 | Olivier |
| 7,985,337 B2 | 7/2011 | Hauser et al. |
| 7,993,531 B2 | 8/2011 | Oleskiewicz et al. |
| 7,993,847 B2 | 8/2011 | Togawa et al. |
| 8,052,632 B2 | 11/2011 | Ghelli et al. |
| 8,052,667 B2 | 11/2011 | Rosiello et al. |
| 8,057,377 B2 | 11/2011 | Holmes et al. |
| 8,057,670 B2 | 11/2011 | Zia et al. |
| 8,057,672 B2 | 11/2011 | Chung et al. |
| 8,123,940 B2 | 2/2012 | Sumian et al. |
| 8,136,676 B2 | 3/2012 | Mizomoto et al. |
| RE43,310 E | 4/2012 | Ishida et al. |
| 8,173,027 B2 | 5/2012 | Hogberg et al. |
| 8,206,331 B2 | 6/2012 | Gura et al. |
| 8,236,184 B2 | 8/2012 | Holmes et al. |
| 8,262,640 B2 | 9/2012 | Zia et al. |
| 8,277,406 B2 | 10/2012 | Felt et al. |
| 8,287,742 B2 | 10/2012 | Holmes |
| 8,288,116 B2 | 10/2012 | Chen |
| 8,336,717 B2 | 12/2012 | Zia |
| 8,337,700 B1 | 12/2012 | Zuk, Jr. |
| 8,349,254 B2 | 1/2013 | Hoshino |
| 8,361,320 B2 | 1/2013 | Zuk, Jr. |
| 8,409,316 B2 | 4/2013 | Nelson et al. |
| 8,425,448 B2 | 4/2013 | Felt et al. |
| 8,439,889 B2 | 5/2013 | Sano |
| 8,460,267 B2 | 6/2013 | Hirabuki |
| 8,486,174 B2 | 7/2013 | Gieseke et al. |
| 8,496,833 B2 | 7/2013 | Kobayashi |
| 8,501,008 B2 | 8/2013 | Lemke et al. |
| 8,517,967 B2 | 8/2013 | Rosiello et al. |
| 8,524,090 B2 | 9/2013 | Oka |
| 8,540,879 B2 | 9/2013 | Heim |
| 8,541,538 B2 | 9/2013 | Nakao et al. |
| 8,551,375 B2 | 10/2013 | Brown et al. |
| 8,597,223 B2 | 12/2013 | Dumon D'Ayot et al. |
| 8,640,738 B2 | 2/2014 | Zia et al. |
| 2001/0027946 A1 | 10/2001 | Fukuda |
| 2002/0030002 A1 | 3/2002 | Verkaart |
| 2002/0053548 A1 | 5/2002 | Lee et al. |
| 2002/0058030 A1 | 5/2002 | Monroy et al. |
| 2003/0057147 A1 | 3/2003 | Sutcliffe et al. |
| 2003/0062299 A1 | 4/2003 | Lee et al. |
| 2003/0146150 A1 | 8/2003 | Hayashi |
| 2003/0150793 A1 | 8/2003 | Verpoort |
| 2003/0209479 A1 | 11/2003 | Lynn et al. |
| 2004/0077831 A1 | 4/2004 | Chapmann et al. |
| 2004/0142316 A1 | 7/2004 | Owen et al. |
| 2004/0178140 A1 | 9/2004 | Bell et al. |
| 2004/0251195 A1 | 12/2004 | Oka et al. |
| 2005/0137517 A1 | 6/2005 | Blickhan et al. |
| 2005/0148748 A1 | 7/2005 | Tanaka et al. |
| 2005/0252821 A1 | 11/2005 | Azzolini et al. |
| 2005/0287124 A1 | 12/2005 | Watanabe et al. |
| 2006/0016753 A1 | 1/2006 | Sowemimo-Coker et al. |
| 2006/0054557 A1 | 3/2006 | Hori et al. |
| 2006/0086666 A1 | 4/2006 | Mari et al. |
| 2006/0086675 A1 | 4/2006 | Purdum et al. |
| 2006/0108272 A1 | 5/2006 | Ariagno et al. |
| 2006/0128016 A1 | 6/2006 | Tokushima et al. |
| 2006/0180526 A1 | 8/2006 | Sugawara et al. |
| 2006/0180542 A1 | 8/2006 | Mari et al. |
| 2006/0226090 A1 | 10/2006 | Robinson et al. |
| 2006/0234210 A1 | 10/2006 | Kenan et al. |
| 2007/0029256 A1 | 2/2007 | Nakano et al. |
| 2007/0095764 A1 | 5/2007 | Yang et al. |
| 2007/0118063 A1 | 5/2007 | Gibbs et al. |
| 2007/0119780 A1 | 5/2007 | Zia et al. |
| 2007/0175816 A1 | 8/2007 | Verpoort |
| 2007/0212674 A1 | 9/2007 | Spiers et al. |
| 2008/0011691 A1 | 1/2008 | Yamada et al. |
| 2008/0023394 A1 | 1/2008 | Naruse et al. |
| 2008/0050275 A1 | 2/2008 | Bischof et al. |
| 2008/0073294 A1 | 3/2008 | Zambianchi et al. |
| 2008/0110829 A1 | 5/2008 | Kobayashi et al. |
| 2008/0147240 A1 | 5/2008 | Kobayashi et al. |
| 2008/0156728 A1 | 7/2008 | Blickhan et al. |
| 2008/0223798 A1 | 9/2008 | Paretta et al. |
| 2008/0260710 A1 | 10/2008 | Kusunoki et al. |
| 2009/0036322 A1 | 2/2009 | Bradley et al. |
| 2009/0071905 A1 | 3/2009 | Goudaliez et al. |
| 2009/0159522 A1 | 6/2009 | Marmey et al. |
| 2009/0173685 A1 | 7/2009 | Imai et al. |
| 2009/0194489 A1 | 8/2009 | Vandlik et al. |
| 2009/0272701 A1 | 11/2009 | Holmes et al. |
| 2009/0324567 A1 | 12/2009 | Spiers et al. |
| 2010/0025335 A1 | 2/2010 | Shimagaki et al. |
| 2010/0062412 A1 | 3/2010 | Nirasawa et al. |
| 2010/0081985 A1 | 4/2010 | Pittinger et al. |
| 2010/0084332 A1 | 4/2010 | Lynn et al. |
| 2010/0108596 A1 | 5/2010 | Duhaut et al. |
| 2010/0136677 A1 | 6/2010 | Delaronde-Wilton et al. |
| 2010/0270232 A1 | 10/2010 | Iwanaga et al. |
| 2010/0291629 A1 | 11/2010 | Fournier-Wirth et al. |
| 2011/0031191 A1 | 2/2011 | Fukuda et al. |
| 2011/0084017 A1* | 4/2011 | Pocher ............. B01D 39/1623 210/490 |
| 2011/0136096 A1 | 6/2011 | Hassanein et al. |
| 2011/0152740 A1 | 6/2011 | Gibbs et al. |
| 2011/0192798 A1 | 8/2011 | Goudaliez et al. |
| 2011/0238029 A1 | 9/2011 | Biset et al. |
| 2011/0240549 A1 | 10/2011 | Andou et al. |
| 2012/0015794 A1 | 1/2012 | Holmes et al. |
| 2012/0024779 A1 | 2/2012 | Ochiai et al. |
| 2012/0067810 A1 | 3/2012 | Yokomizo et al. |
| 2012/0067811 A1 | 3/2012 | Yokomizo et al. |
| 2012/0111807 A1 | 5/2012 | Hillyer et al. |
| 2012/0115124 A1 | 5/2012 | Yoshida et al. |
| 2012/0135391 A1 | 5/2012 | Shaz et al. |
| 2012/0141975 A1 | 6/2012 | Sato et al. |
| 2012/0160763 A1 | 6/2012 | Yokomizo et al. |
| 2012/0160782 A1 | 6/2012 | Yokomizo et al. |
| 2012/0165176 A1 | 6/2012 | Andou et al. |
| 2012/0171658 A1 | 7/2012 | Bein et al. |
| 2012/0175313 A1 | 7/2012 | Barry et al. |
| 2012/0175319 A1 | 7/2012 | Cotton et al. |
| 2012/0228207 A1 | 9/2012 | Mathias et al. |
| 2012/0258459 A1 | 10/2012 | Huang et al. |
| 2012/0263771 A1 | 10/2012 | Carlson et al. |
| 2012/0269679 A1 | 10/2012 | Payrat et al. |
| 2012/0289926 A1 | 11/2012 | Hirabuki et al. |
| 2012/0294826 A1 | 11/2012 | Spitalnik et al. |
| 2012/0315664 A1 | 12/2012 | Friedrich et al. |
| 2013/0001149 A1 | 1/2013 | Yamamoto et al. |
| 2013/0004937 A1 | 1/2013 | Yoshida et al. |
| 2013/0005557 A1 | 1/2013 | Yokomizo et al. |
| 2013/0005558 A1 | 1/2013 | Inadome et al. |
| 2013/0046225 A1 | 2/2013 | Nose et al. |
| 2013/0047861 A1 | 2/2013 | Yoshida et al. |
| 2013/0092319 A1 | 4/2013 | Lynn et al. |
| 2013/0140228 A1 | 6/2013 | Schwender et al. |
| 2013/0150793 A1 | 6/2013 | Beissel et al. |
| 2013/0153482 A1 | 6/2013 | Gibbs et al. |
| 2013/0264288 A1 | 10/2013 | Hlavinka et al. |
| 2013/0323711 A1 | 12/2013 | Singh et al. |
| 2013/0345674 A1 | 12/2013 | Kusters et al. |
| 2015/0265755 A1 | 9/2015 | Lynn et al. |
| 2015/0265758 A1 | 9/2015 | Verri et al. |
| 2015/0265954 A1 | 9/2015 | Lynn et al. |

FOREIGN PATENT DOCUMENTS

| | | |
|---|---|---|
| DE | 37 34 170 A1 | 4/1989 |
| DE | 40 19 114 A1 | 10/1991 |
| DE | 40 22 700 A1 | 1/1992 |
| DE | 93 11 251 U1 | 10/1993 |
| DE | 43 41 005 A1 | 6/1995 |
| DE | 296 03 873 U1 | 6/1996 |

(56) References Cited

FOREIGN PATENT DOCUMENTS

| | | |
|---|---|---|
| DE | 197 33 407 A1 | 2/1999 |
| DE | 102 39 658 A1 | 11/2003 |
| DE | 103 15 484 A1 | 8/2004 |
| EP | 0 370 584 A1 | 5/1990 |
| EP | 0 406 485 A1 | 1/1991 |
| EP | 0 408 462 B1 | 1/1991 |
| EP | 0 516 846 A1 | 12/1992 |
| EP | 0 526 678 A1 | 2/1993 |
| EP | 0 573 405 A1 | 12/1993 |
| EP | 0 606 646 B1 | 9/1997 |
| EP | 0 792 677 A1 | 9/1997 |
| EP | 0958838 A2 | 11/1999 |
| EP | 0 728 491 B1 | 11/2000 |
| EP | 1 048 305 A2 | 11/2000 |
| EP | 0 888 789 B1 | 9/2002 |
| EP | 1300128 A1 | 4/2003 |
| EP | 1300168 A1 | 4/2003 |
| EP | 1 484 390 A1 | 12/2004 |
| EP | 1 611 907 A1 | 1/2006 |
| EP | 0 933 090 B1 | 7/2006 |
| EP | 1 897 571 A1 | 3/2008 |
| EP | 1 902 740 A1 | 3/2008 |
| EP | 0 976 413 B1 | 4/2008 |
| EP | 1 925 328 A2 | 5/2008 |
| EP | 0 953 361 B1 | 2/2013 |
| EP | 1 838 412 B1 | 5/2013 |
| FR | 2 821 762 A1 | 9/2002 |
| GB | 1300850 A | 12/1972 |
| GB | 1302564 A | 1/1973 |
| GB | 2473621 A | 3/2011 |
| IE | 2009/0703 | 6/2011 |
| JP | 2007014854 | 1/2007 |
| WO | WO 88/002264 A1 | 4/1988 |
| WO | WO 89/002304 A1 | 3/1989 |
| WO | WO 90/000059 A1 | 1/1990 |
| WO | WO 95/000631 A1 | 1/1995 |
| WO | WO 95/017234 A1 | 6/1995 |
| WO | WO 98/028057 A1 | 7/1998 |
| WO | WO 99/013925 A1 | 3/1999 |
| WO | WO 99/016480 A1 | 4/1999 |
| WO | WO 99/039758 A1 | 8/1999 |
| WO | WO 99/044718 A1 | 9/1999 |
| WO | WO 99/053975 A1 | 10/1999 |
| WO | WO 00/020053 A1 | 4/2000 |
| WO | WO 00/053287 A1 | 9/2000 |
| WO | WO 00/054824 A1 | 9/2000 |
| WO | WO 00/062840 A1 | 10/2000 |
| WO | WO 01/032828 A2 | 5/2001 |
| WO | WO 01/036022 A1 | 5/2001 |
| WO | WO 02/011855 A1 | 2/2002 |
| WO | WO 02/024256 A1 | 3/2002 |
| WO | WO 03/047655 A1 | 6/2003 |
| WO | WO 06/003350 A1 | 1/2006 |
| WO | WO 07/025738 A2 | 3/2007 |
| WO | WO 07/054638 A1 | 5/2007 |
| WO | WO 08/092610 A1 | 8/2008 |
| WO | WO 08/103142 A1 | 8/2008 |
| WO | WO 09/005046 A1 | 1/2009 |
| WO | WO 09/057574 A1 | 5/2009 |
| WO | WO 10/004104 A2 | 1/2010 |
| WO | WO 10/026891 A1 | 3/2010 |
| WO | WO 10/136447 A1 | 12/2010 |
| WO | WO 11/125617 A1 | 10/2011 |
| WO | WO 11/157822 A1 | 12/2011 |
| WO | WO 12/017291 A2 | 2/2012 |
| WO | WO 12/057029 A1 | 5/2012 |
| WO | WO 12/090834 A1 | 7/2012 |
| WO | WO 12/090835 A1 | 7/2012 |
| WO | WO 12/093179 A1 | 7/2012 |
| WO | WO 12/139209 A1 | 10/2012 |
| WO | WO 13/022491 A1 | 2/2013 |

OTHER PUBLICATIONS

Partial International Search Report dated Dec. 1, 2014 for PCT/US2014/041217.
Partial International Search Report dated Nov. 18, 2014 for PCT/US2014/041210.
International Search Report and Written opinion dated Feb. 5, 2015 for PCT/US2014/041210.
USPTO Office Action dated Mar. 22, 2018 for U.S. Appl. No. 15/128,331.
USPTO Office Action dated Sep. 8, 2017 for U.S. Appl. No. 15/128,331.

* cited by examiner

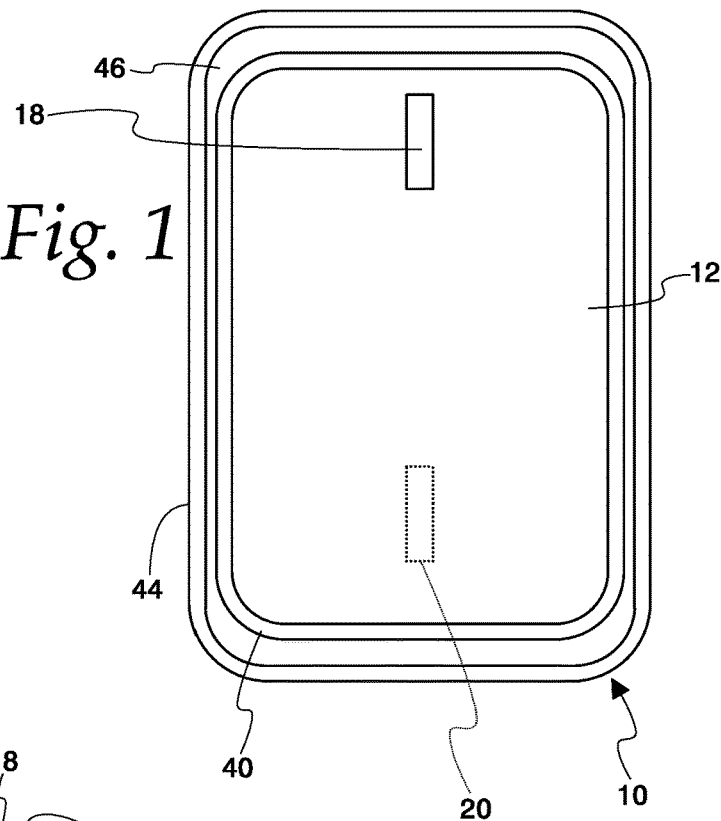
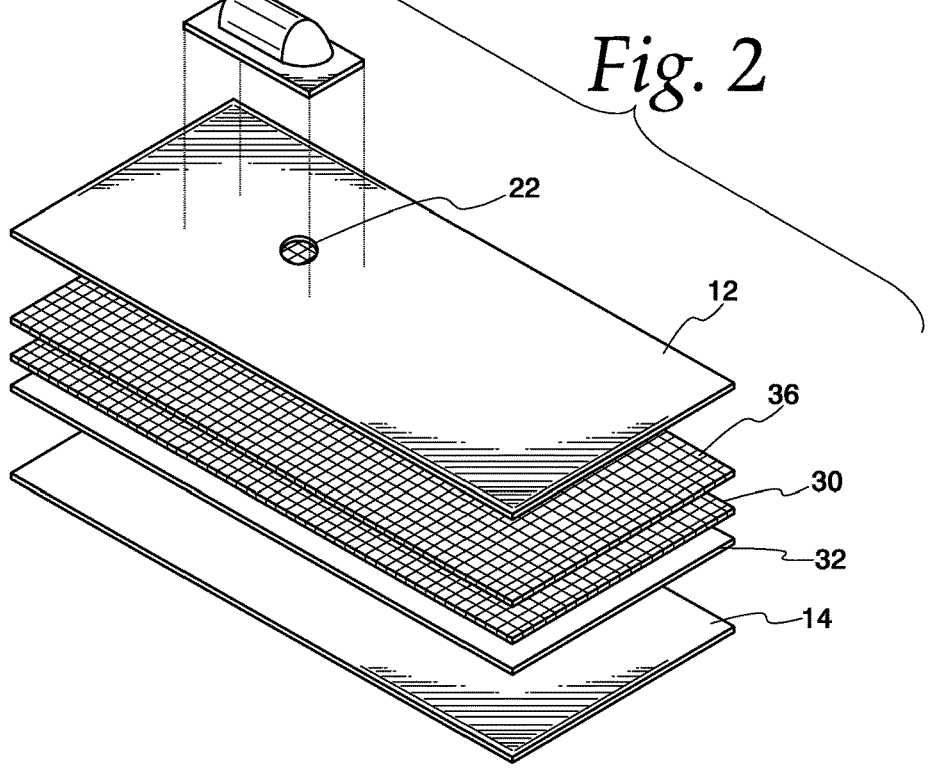

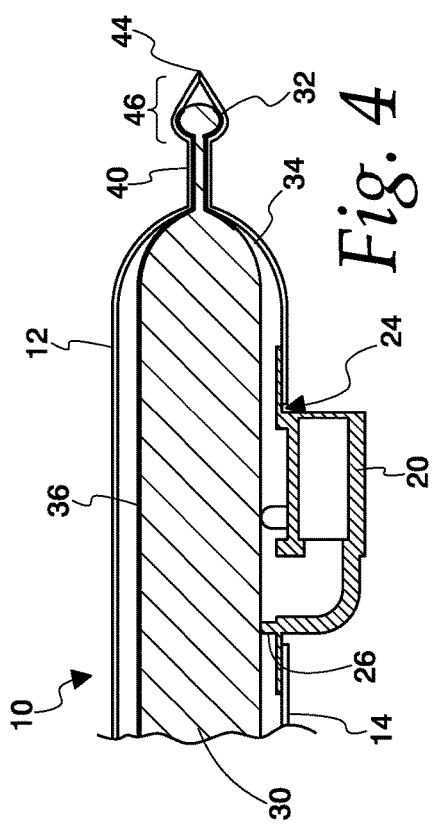
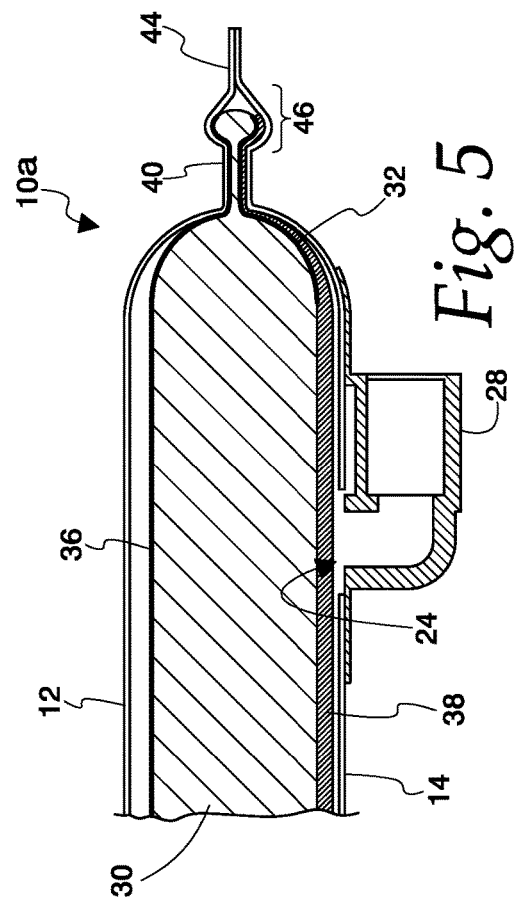
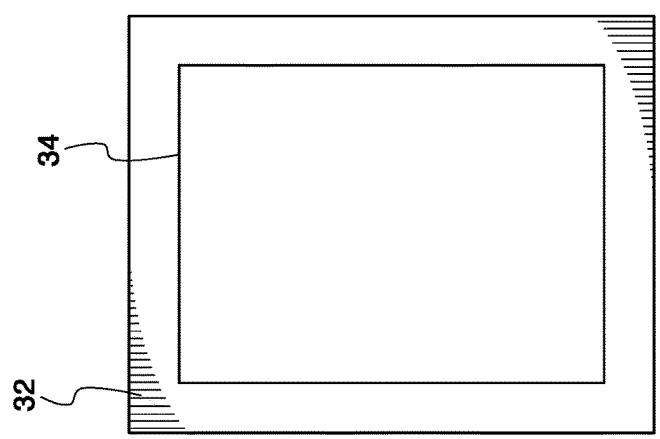

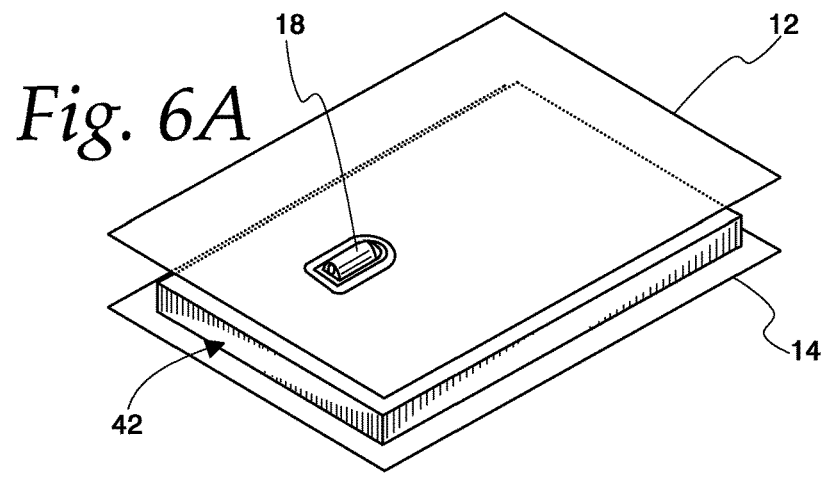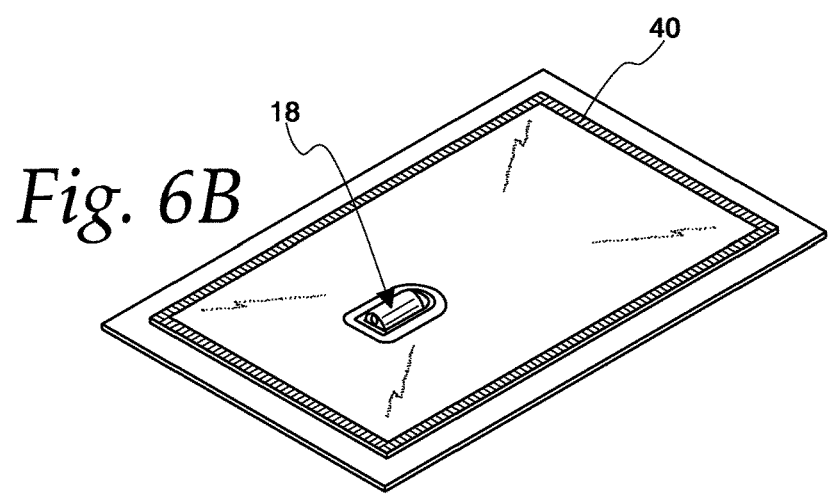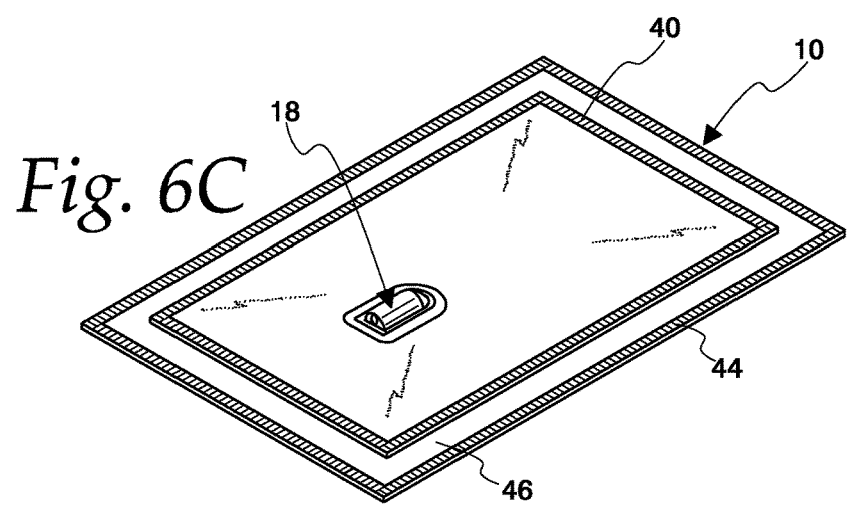

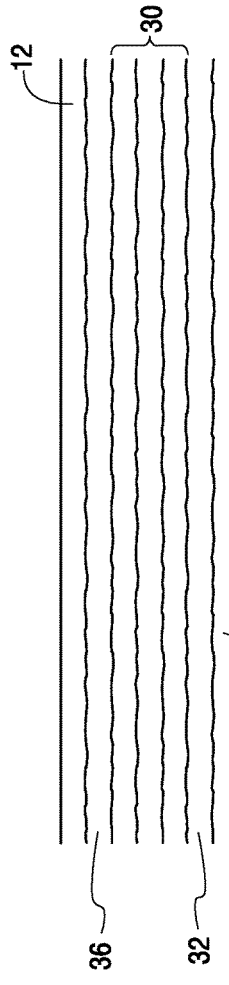
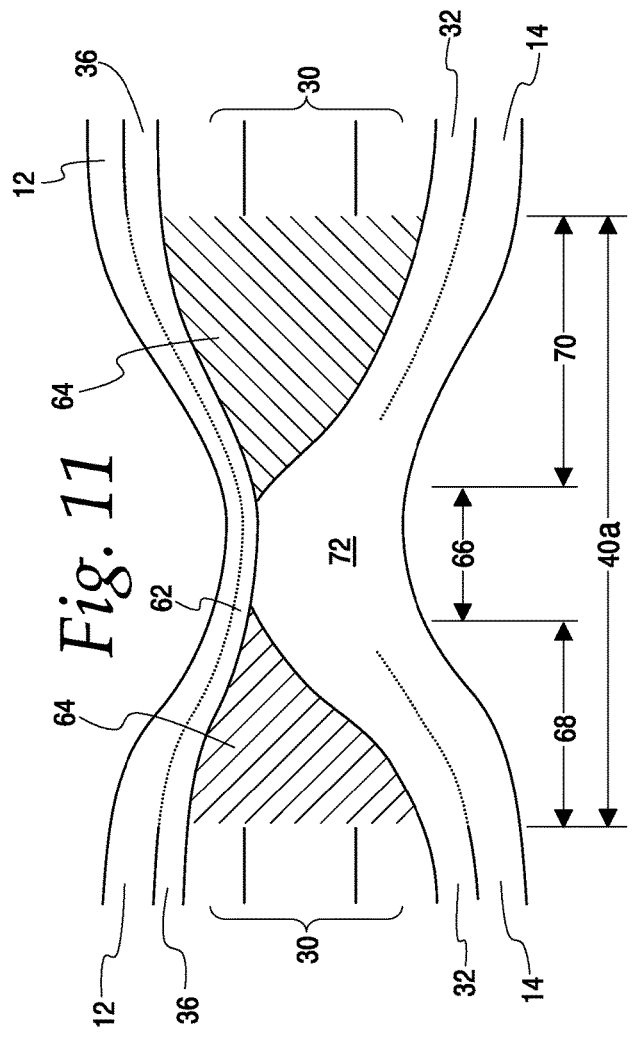
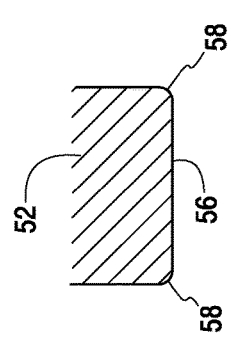
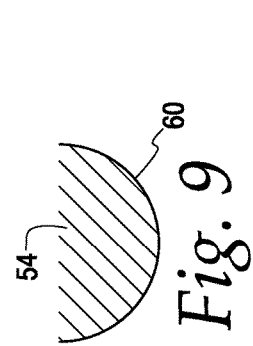
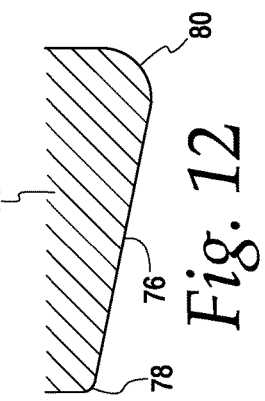

FLEXIBLE BIOLOGICAL FLUID FILTERS

RELATED APPLICATION

This application is a U.S. national stage application of PCT Patent Application Serial No. PCT/US2014/041210, filed Jun. 6, 2014, which is a continuation-in-part of U.S. patent application Ser. No. 14/222,961, filed Mar. 24, 2014, the contents of which are incorporated by reference herein.

DESCRIPTION

Technical Field

The present disclosure generally relates to filters used in the collection and processing of blood and blood components or other biological fluids. More particularly, the present disclosure relates to flexible "soft housing" filters and methods for manufacturing such filters.

BACKGROUND

Using various manual and automated systems and methods, whole blood is collected and separated into its clinical components (typically red blood cells, platelets, and plasma). The collected components are typically individually stored and used to treat a variety of specific conditions and diseased states.

Before transfusing the collected blood components to a recipient in need of the components, or before subjecting blood components to treatment (such as, but not limited to, pathogen inactivation), it is often desirable to minimize the presence of impurities or other materials that may cause undesired side effects in the recipient. For example, because of possible reactions, it is generally considered desirable to reduce the number of leukocytes in blood components before storage, or at least before transfusion (i.e., "leukoreduction").

Filters are widely used to accomplish leukoreduction in blood products today (e.g., warm and cold filtration of leukocytes from whole blood, red cells, and/or platelet products). Filters typically include a filter media disposed between mating walls of a filter housing. Inlet and outlet ports associated with the housing provide flow paths to and from the interior of the filter. The walls of the housing may be made of a rigid, typically plastic, material, although filters including soft housings are also known. Soft housing filters provide the advantage of being able to withstand handling and centrifuging without breakage of the filter. Examples of soft housing filters are disclosed in U.S. Pat. Nos. 6,367,634; 6,422,397; 6,745,902; 7,353,956; 7,332,096; 7,278,541; and U.S. Patent Application Publication No. 2003/0209479, all of which are hereby incorporated by reference herein. Due to the importance of filtering blood or blood components, there exists an ongoing desire to improve the construction, performance, and manufacturability of biological fluid filters.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a biological fluid filter assembly is provided. The filter assembly includes a flexible housing having first and second walls. A filtration medium is at least partially positioned between the first and second walls of the housing. A seal passes through the filtration medium to define a perimeter within the biological fluid filter assembly and joins the first and second walls of the housing, with there being substantially no filtration medium present in a central section of the seal along at least a majority of the extent of the perimeter defined by the seal.

In another aspect, a biological fluid filter assembly is provided. The filter assembly includes a flexible housing having first and second walls. A filtration medium is at least partially positioned between the first and second walls of the housing. A post-filter mesh is at least partially positioned between the filtration medium and the second housing wall. A seal joins the first and second walls of the housing.

In yet another aspect, a biological fluid filter assembly is provided. The filter assembly includes a flexible housing having first and second walls, the first wall including an inlet port and the second wall including an outlet port, with the first and second walls being made of a plastic material. A filtration medium for removing at least one substance from a biological fluid is at least partially positioned between the inlet and outlet ports, with a pre-filter at least partially positioned between the inlet port and the filtration medium. A mesh element having a mesh integrally formed with a frame is at least partially positioned between the outlet port and the filtration medium, with the mesh element being made of the plastic material. A seal is formed by integrating a section of the filtration medium at or adjacent to its perimeter, a section of the pre-filter at or adjacent to its perimeter, a section of the frame of the mesh element, and a section of the first and second walls at or adjacent to their perimeter and over their entire perimeter. The seal includes a central section consisting of a layer consisting only of the plastic material of the first wall and having a thickness in the range of approximately 90-100 micrometers, an intermingled layer in which the plastic material of at least the first wall is intermingled with the pre-filter and having a thickness in the range of approximately 170-200 micrometers, and an aggregate in which the plastic material of at least the second wall and the frame are intermingled and having a thickness in the range of approximately 840-900 micrometers.

In another aspect, a biological fluid filter assembly is provided. The filter assembly includes a flexible housing having first and second walls. A filtration medium is at least partially positioned between the first and second walls of the housing. A post-filter mesh is at least partially positioned between the filtration medium and the second housing wall and has a normalized air permeability at a pressure difference of 125 Pa in the range of approximately 40 to approximately 800 cm$^2$/s. More preferably, the normalized air permeability at a pressure difference of 125 Pa is in a range of approximately 50 cm$^2$/s-400 cm$^2$/s or, even more preferably, in a range of approximately 70 cm$^2$/s-150 cm$^2$/s. A seal joins the first and second walls of the housing.

In another aspect, a method is provided for manufacturing a biological fluid filter assembly. The method includes providing a first flexible housing wall and a second flexible housing wall. At least a portion of a filtration medium is positioned between the housing walls. A seal that passes through the filtration medium is formed to join the housing walls and define a perimeter within the biological fluid filter assembly, with there being substantially no filtration medium present in a central section of the seal along at least a majority of the extent of the perimeter defined by the seal.

BRIEF DESCRIPTION OF THE DRAWINGS

FIG. 1 is a front elevational view of a biological fluid filter assembly according to an aspect of the present disclosure;

FIG. 2 is a perspective, exploded view of the biological fluid filter assembly of FIG. 1;

FIG. 3 is a front elevational view of a support member of the biological fluid filter assembly of FIG. 1;

FIG. 4 is a side cross-sectional view of a portion of the biological fluid filter assembly of FIG. 1;

FIG. 5 is a side cross-sectional view of a portion of another embodiment of a biological fluid filter assembly according to an aspect of the present disclosure;

FIGS. 6A-6C illustrate steps of an exemplary process for manufacturing biological fluid filter assemblies according to the present disclosure;

FIG. 8 is a cross-sectional view of a sealing die according to known design that may be used to form an inner seal of a biological fluid filter assembly according to the present disclosure;

FIG. 9 is a cross-sectional view of a sealing die that may be used to form an inner seal substantially omitting filtration medium in a section thereof;

FIG. 10 is a detail view of a section of a biological fluid filter assembly prior to forming an inner seal;

FIG. 11 is a cross-sectional view of the section of the biological fluid filter assembly of FIG. 10, after having formed an inner seal substantially omitting filtration medium in a section thereof; and FIG. 12 is a cross-sectional view of an alternative sealing die that may be used to form an inner seal substantially omitting filtration medium in a section thereof.

DETAILED DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

Figure 7A:
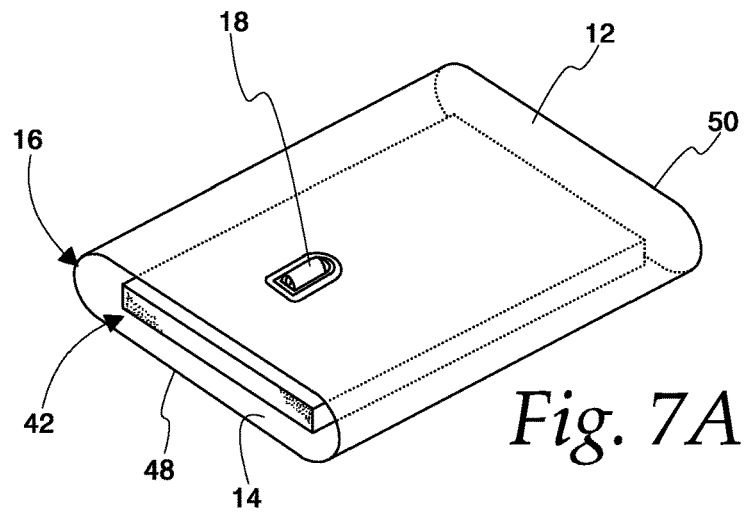
FIGS. 7A-7C illustrate steps of another exemplary process for manufacturing biological fluid filter assemblies according to the present disclosure.

FIG. 1 shows an exemplary embodiment of a biological fluid filter assembly 10 according to the present disclosure. As shown in FIG. 1, the filter assembly 10 may include an outer housing having first and second sides or walls 12 and 14 (FIGS. 2 and 4), which may correspond to inlet and outlet sides for fluid flowing through the filter assembly 10. In one embodiment, the first and second walls 12 and 14 of the filter housing may be separate sheets of flexible material (FIGS. 2 and 6A-6C), which may be formed of a polyvinyl chloride ("PVC") material or any other suitable material (preferably a flexible, medical grade plastic material) through which the biological fluid will not flow. In another embodiment, the first and second walls 12 and 14 of the filter housing may be opposing faces of a generally tubular piece of material 16 (FIGS. 7A-7C) or two portions of a single sheet of material that is folded onto itself.

Preferably, the inlet or first side 12 of the filter housing is provided with an inlet port 18 (FIGS. 1 and 2) and the outlet or second side 14 of the filter housing is provided with an outlet port 20 (FIGS. 1 and 4), with the ports 18 and 20 positioned at least partially outside of the filter assembly 10 for connection to other components of a fluid processing set by tubing or the like. The inlet and outlet ports 18 and 20 may be secured to their associated walls of the filter housing by any suitable means (e.g., being heat sealed thereto using radio-frequency energy). The walls 12 and 14 of the filter housing are preferably each provided with an opening or aperture with which the associated port communicates to allow fluid flow into and out of the filter assembly 10. FIG. 2 shows an opening 22 formed in the first wall 12 and FIG. 4 shows an opening 24 formed in the second wall 14 of the filter housing.

In the embodiment of FIG. 4, the outlet port 20 includes an extension or projection or formation or spacer 26 which passes through the associated opening 24 and into an interior of the filter assembly 10. If provided, the spacer 26 may serve to space or separate the outlet side 14 of the filter housing from an interior component of the filter assembly 10 (such as a filtration medium) to prevent the interior component from being pulled into contact with the outlet side 14 during filtration (due to a pressure differential), which can hinder fluid flow through the filter assembly 10. Alternatively, an outlet port 28 may be provided without a spacer (FIG. 5), in which case the filter assembly may or may not include a separate spacer positioned within the filter assembly, adjacent to the outlet side 14 of the filter housing to separate the outlet side 14 from an interior component of the filter assembly.

The inlet and outlet ports 18 and 20, 28 are preferably relatively rigid compared to the filter housing, and may comprise molded components formed of a plastic material, although other materials and manufacturing methods may be employed without departing from the scope of the present disclosure.

A filtration medium 30 (FIGS. 2 and 4) is at least partially positioned between the two walls 12 and 14 of the filter housing. Preferably, the filtration medium 30 is fully positioned within the filter housing when the filter assembly 10 is fully assembled, as in FIG. 1.

The filtration medium 30 may be variously configured, depending on the nature of the substance(s) to be removed or separated from the biological fluid passed through the filter assembly 10. For example, the filtration medium 30 may be configured to remove a substance or substances from a biological fluid by depth filtration or by a binding material that retains the targeted substance(s) while allowing the other components of the biological fluid to flow through the filtration medium 30. In an exemplary embodiment, the filtration medium 30 is configured to separate leukocytes from blood or a blood component or some other leukocyte-containing fluid by depth filtration, in which case the filtration medium 30 may be formed of a fibrous or non-fibrous material having pores sized to trap leukocytes within the filter assembly 30, while allowing other components of the biological fluid to pass through. The filtration medium 30 may be formed of any suitable material but, in one exemplary embodiment, is formed of a melt-blown, nonwoven, fibrous material, such as a polybutylene terephthalate ("PBT") material.

In one embodiment, the filtration medium 30 is formed from a plurality of layers, which may be either substantially identical or differently configured. For example, a multi-layer filtration medium may be comprised of a plurality of fibrous layers, a plurality of non-fibrous layers, or a combination of fibrous layers and non-fibrous layers. While a multi-layer filtration medium may be preferred for improved filtration performance, it is also within the scope of the present disclosure for the filtration medium to be a single-layer component.

In addition to a filtration medium 30, at least a portion of a support member may also be positioned between the walls 12 and 14 of the filter housing. Preferably, the support member is fully positioned within the filter housing when the filter assembly 10 is fully assembled (as in FIG. 1), between the filtration medium 30 and the outlet or second side 14 of the filter housing.

The support member may be variously configured, but in the embodiment of FIGS. 1-4, the support member is provided as a frame 32. The frame 32 may be variously configured, but is preferably configured as a planar or sheet-like component with an outer perimeter having a shape that is congruent to the filtration medium 30. FIG. 3 illustrates an embodiment of a frame 32 having a generally rectangular outer perimeter, which matches the generally rectangular configuration of the associated filtration medium 30. While it may be preferred for the perimeter of the frame 32 to be substantially the same size and shape as the associated filtration medium 30, it is also within the scope of the present disclosure for the perimeter of the frame 32 to be differently sized (typically larger) and shaped from the associated filtration medium 30.

As shown in FIG. 3, the frame 32 may define an opening or aperture 34, which may be centrally or non-centrally located and either the same shape as the outer perimeter of the frame 32 (as in FIG. 3) or a different shape. In other embodiments, the frame may define a plurality of openings or apertures, which may be similarly or differently configured. In a preferred embodiment, the frame 32 is formed of a material through which the biological fluid being filtered will not pass, in which case the opening 34 or openings allow for the flow of fluid through the frame 32.

As described above, the frame 32 may be formed of a material through which the biological fluid being filtered will not flow. In one embodiment, the frame 32 is formed of a PVC material (e.g., the same material as is used to form the housing), but other materials may be employed without departing from the scope of the present disclosure. The frame 32 may be provided as a single-sheet or single-piece component or as a multi-sheet or multi-piece, stacked component.

The filter assembly 10 may include additional components positioned between the walls 12 and 14 of the housing. In the embodiment of FIGS. 1-2 and 4, the filter assembly 10 includes a pre-filter 36 at least partially positioned between the walls 12 and 14 of the filter housing. Preferably, the pre-filter 36 is fully positioned within the filter housing when the filter assembly 10 is fully assembled (as in FIG. 1), between the filtration medium 30 and the inlet or first side 12 of the filter housing.

The pre-filter 36 may be variously configured, but is preferably configured as a planar or sheet-like component with a shape that is congruent to the filtration medium 30. In the illustrated embodiment, the pre-filter 36 has a generally rectangular configuration, which matches the generally rectangular configuration of the associated filtration medium 30 and frame 32. While it may be preferred for the perimeter of the pre-filter 36 to be substantially the same size and shape as the filtration medium 30, it is also within the scope of the present disclosure for the perimeter of the pre-filter 36 to be differently sized and shaped from the perimeter of the associated filtration medium 30.

The pre-filter 36 is configured to allow the passage of biological fluid therethrough. Preferably, the pre-filter 36 has different filtration properties (e.g., porosity) than the associated filtration medium 30. In one embodiment, the pre-filter 36 has larger pores than the associated filtration medium 30. If the filter assembly 10 is provided as a leukofilter, the pre-filter 36 may be configured to remove microaggregates from the biological fluid prior to the fluid encountering the filtration medium 30. In such an application, it may be advantageous for the pre-filter 36 to be comprised of a polyethylene terephthalate ("PET") material. In other applications, other material compositions may be employed. The pre-filter 36 may be provided as a single-sheet or single-piece component or as a multi-sheet or multi-piece, stacked component.

In an alternative embodiment, which is illustrated in FIG. 5, the filter assembly 10a includes the same components as the embodiment of FIGS. 1-4, but with an additional post-filter 38 at least partially positioned between the walls 12 and 14 of the filter housing. Preferably, the post-filter 38 is fully positioned within the filter housing when the filter assembly 10a is fully assembled. The post-filter 38 may be variously secured within the filter housing, such as being secured between the frame 32 and the outlet or second side 14 of the filter housing. Alternatively, the post-filter may be positioned or seated within the opening 34 defined by the frame 32, as in the embodiment of FIG. 3A. Preferably, the post-filter occupies the entirety of the opening 34, but it is also within the scope of the present disclosure for the post-filter to occupy only a portion of the opening 34. If the post-filter is mounted within the opening 34 of the frame 32, the outer perimeter of the post-filter may be secured to the frame 32 by adhesion or a weld or a mechanical fastener or any other suitable fixation means.

The post-filter 38 may be variously configured, but is preferably configured as a planar or sheet-like component with a shape that is congruent to the frame 32. In the illustrated embodiment, the post-filter 38 has a generally rectangular configuration, which matches the generally rectangular configuration of the associated filtration medium 30 and frame 32. While it may be preferred for the post-filter 38 to be substantially the same size and shape as the outer perimeter of the frame 32, it is also within the scope of the present disclosure for the post-filter 38 to be differently sized and shaped from the perimeter of the associated frame 32.

The post-filter 38 is configured to allow the passage of biological fluid therethrough. The post-filter 38 may have filtration properties (e.g., porosity) that are either the same as or different from those of the associated filtration medium 30. In one embodiment, the post-filter 38 is formed of the same material as the associated filtration medium 30 (e.g., PBT), in which case the post-filter 38 may be distinguished from the filtration medium 30 by the presence of the frame 32 positioned therebetween. Depending on the material composition and configuration of the post-filter 38, it may provide any of a number of functions, including filtration-improvement functions (e.g., acting as a spacer or manifold if the associated outlet port omits an inwardly projecting spacer) and/or manufacturability-improvement features. The post-filter 38 may be provided as a single-sheet or single-piece component or as a multi-sheet or multi-piece, stacked component.

Figure 3A:
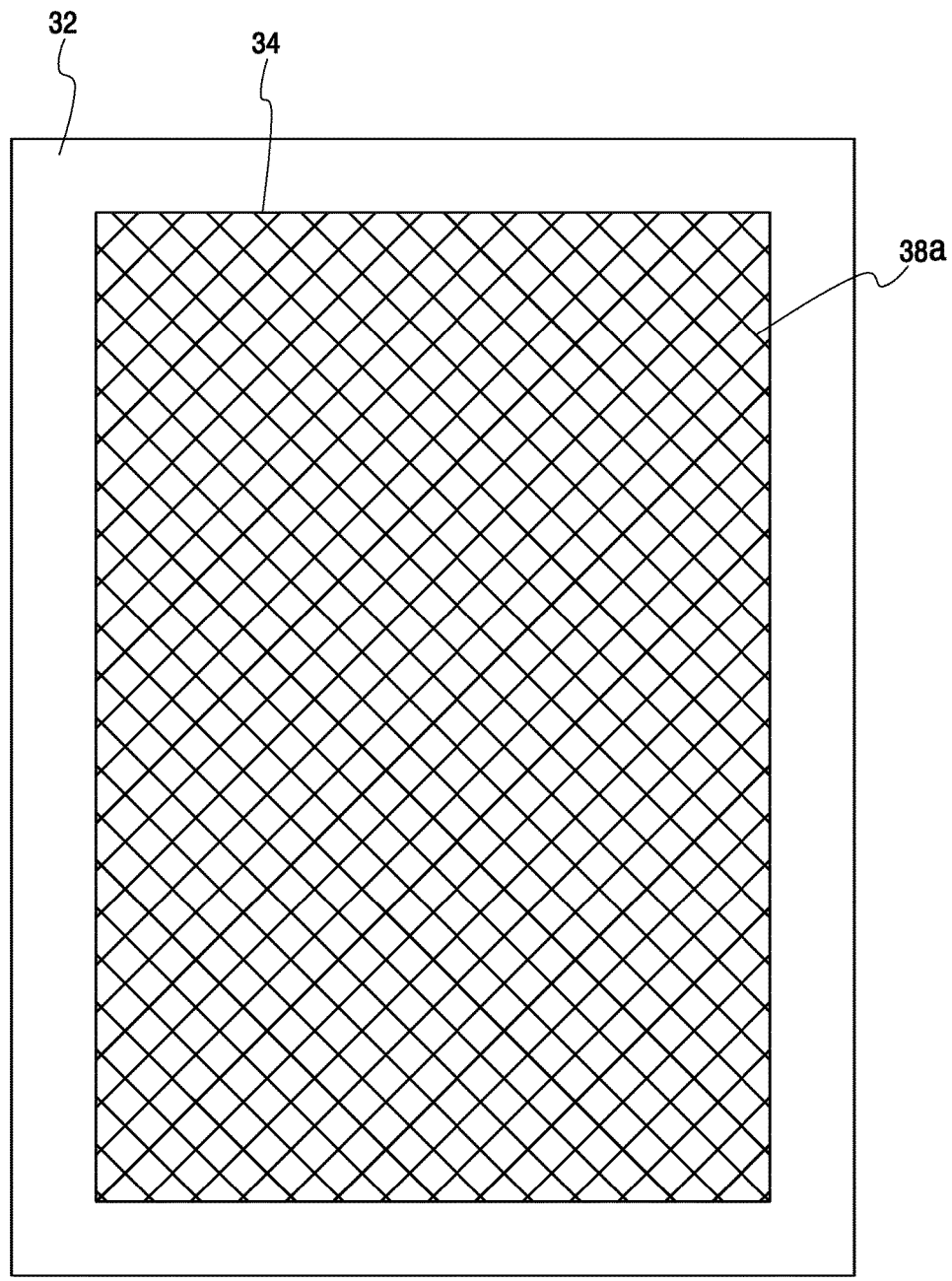
FIG. 3A is a front elevational view of the support member of FIG. 3, incorporating a post-filter.
Figure 3B:
FIG. 3B is a cross-sectional view of a post-filter having a varying thickness according to an aspect of the present disclosure.
Figure 3C:
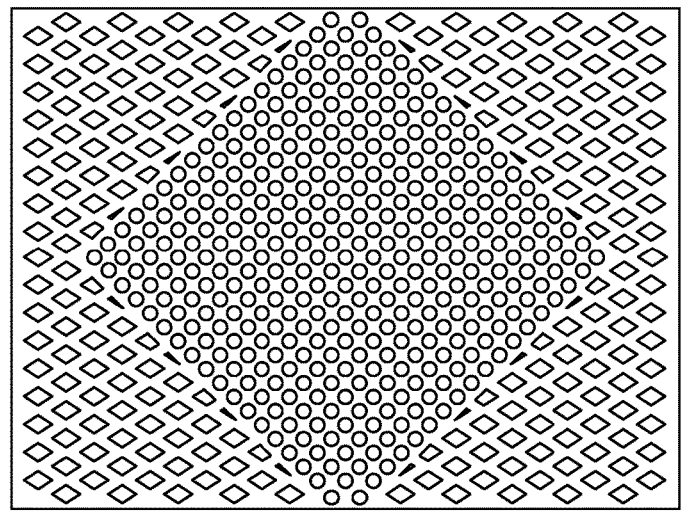
FIG. 3C is a front elevational view of a post-filter having differently configured voids according to an aspect of the present disclosure.
Figure 3D:
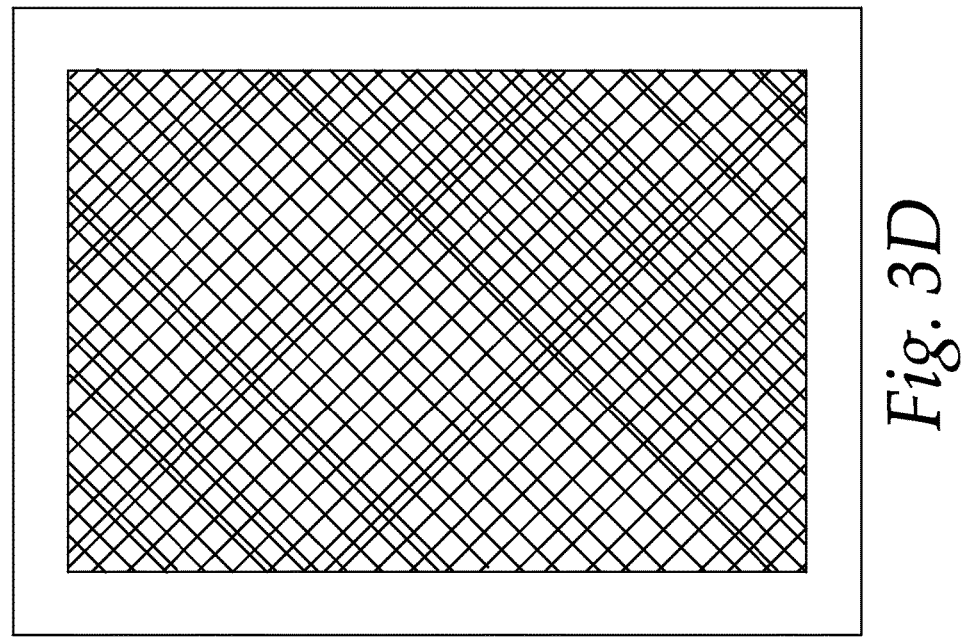
FIG. 3D is a front elevational view of a post-filter having voids arranged in a non-uniform pattern according to an aspect of the present disclosure.

In an alternative embodiment, the post-filter may be provided as a mesh or mesh-like layer. As used herein, the term "mesh" refers to a semi-permeable layer with material present in a grid or web or crossed arrangement, such as shown in FIG. 3A as component 38a. The mesh 38a may be formed according to any suitable method, resulting in a mesh having a varying thickness (referred to herein as a "three-dimensional" mesh), as in FIG. 3B, or a mesh having a generally uniform thickness (referred to herein as a "two-dimensional" or "planar" mesh). If provided as a three-dimensional mesh, the mesh may be formed of overlapping or woven strands or strips of material. If provided as a two-dimensional mesh, the mesh may be defined by non-woven, non-overlapping strands or strips of material present in a plane.

The material of the mesh 38a defines openings or voids through which filtered fluid passes before exiting the filter assembly 10 via the outlet port 20, 28. The mesh 38a of FIG. 3A is shown with generally diamond-shaped openings or voids, but it is within the scope of the present disclosure for the openings or voids to be differently shaped (e.g., a regular shape, such as generally square or rectangular or circular or triangular or pentagonal or hexagonal, or an irregular shape), as in FIG. 3C. A primary purpose of the mesh 38a may be to act as a manifold which separates the filtration medium 30 from the outlet side 14 of the filter housing, while allowing filtered fluid to freely flow from the filtration medium 30 to the outlet port 20, 28. Accordingly, the voids may be relatively large to provide a mesh 38a having a porosity that is greater than the porosity of the filtration medium 30. However, if the voids are too large, it is possible for the outlet side 14 of the filter housing to press against the filtration medium 30 during use, thereby making it more difficult for filtered fluid to flow out of the filter assembly 10. Thus, it may be preferred for the mesh 38a to have an intermediate porosity, with voids that are large enough to allow substantially free flow of filtered fluid out of the filter assembly 10, but not so large as to negate the desired manifold effect. In one exemplary embodiment, the voids are generally rectangular or square or diamond-shaped, each having a height and width in the range of approximately 0.5-20 mm, with the mesh 38a having a thickness in the range of approximately 0.5-4 mm.

Alternatively, rather than characterizing the porosity of the mesh 38a in terms of the size and shape of its voids, it is also possible to characterize its porosity in terms of its permeability properties. For example, at a pressure difference of 125 Pa (1250 dyne/cm$^2$), an approximately 1.6 mm thick mesh 38a according to the present disclosure was measured as having an air permeability of approximately 510 cm$^3$/s·cm$^2$ using an air permeability tester of Frazier Precision Instrument Company of Hagerstown, Md. (although other air permeability testers and test methods may be employed without departing from the scope of the present disclosure). This raw value for a mesh 38a having a thickness of approximately 1.6 mm may be normalized to approximately 81.5 cm$^2$/s, which is the air permeability at a pressure difference of 125 Pa (1250 dyne/cm$^2$) of the same material having a thickness of 1 cm. It may be advantageous for an approximately 1.6 mm thick mesh 38a of the type described herein to have an air permeability in the range of approximately 250 cm$^3$/s·cm$^2$-5000 cm$^3$/s·cm$^2$ at a pressure difference of 125 Pa (1250 dyne/cm$^2$) or a normalized (i.e., for a 1 cm thickness) air permeability at the same pressure difference in a range of approximately 40 cm$^2$/s-800 cm$^2$/s. More preferably, the normalized air permeability at a pressure difference of 125 Pa (1250 dyne/cm$^2$) is in a range of approximately 50 cm$^2$/s-400 cm$^2$/s or, even more preferably, in a range of approximately 70 cm$^2$/s-150 cm$^2$/s. While such normalized air permeabilities may be preferred for a mesh 38a according to the present disclosure, it is also within the scope of the present disclosure for the mesh 38a to have an air permeability that lies outside of (preferably above) these ranges.

The mesh 38a may have a generally uniform porosity or permeability, with generally uniform voids arranged in a uniform pattern, or may have a non-uniform porosity or permeability (FIG. 3D), with differently sized and/or shaped voids in a uniform or non-uniform pattern or generally uniform voids arranged in a non-uniform pattern.

The mesh 38a may be formed of any suitable material or materials such as, but not limited to, PVC. If the filter assembly 10 is provided with both a frame 32 and a mesh 38a, the frame 32 and mesh 38a may be separate components that are joined to each other (e.g., by welding or an adhesive or any other suitable method) prior to being incorporated into the filter assembly 10 or may remain separate. While the frame 32 and mesh 38a may be formed of different materials, the frame 32 and the mesh 38a are preferably formed of the same material, with the two being incorporated together as a unitary or integrated or single component formed by a molding process or any other suitable method. As shown in FIG. 3A, when the filter assembly 10 includes both a frame 32 and a mesh 38a, the mesh 38a is preferably positioned or seated or defined within the opening 34 defined by the frame 32. Preferably, the mesh 38a occupies the entirety of the opening 34, but it is also within the scope of the present disclosure for the mesh 38a to occupy only a portion of the opening 34. The composite frame 32 and mesh 38a component of FIG. 3A may be referred to herein as a mesh element.

In another embodiment, rather than pairing the mesh 38a with a frame 32, a filter assembly may be provided with only a mesh 38a between the filtration medium 30 and the outlet side 14 of the filter housing. If only a mesh 38a is provided, the mesh 38a may be configured to free-float with respect to the other components of the filter assembly (i.e., positioned inward of the seals of the filter assembly) or be fully secured within the filter assembly (e.g., having a perimeter that is fully present within one or more seals of the filter assembly) or be partially secured within the filter assembly (e.g., having only a portion of the perimeter of the mesh 38a positioned within one or more seals of the filter assembly).

The filter assembly 10, 10a includes a seal 40 (FIGS. 1, 4, and 5), which joins the two walls 12 and 14 of the filter housing, as well as the filtration medium 30 and the frame 32. If provided, the seal 40 may also join the other interior components of the filter assembly 10, 10a (i.e., the pre-filter 36 and/or the post-filter 38). The seal 40 may be formed by any suitable sealing process, such as the application of pressure and radio-frequency heating to the two walls 12 and 14 of the filter housing and the interior components of the filter assembly 10, 10a positioned therebetween (collectively identified at 42 in FIG. 6A). Preferably, the seal 40 forms a complete seal at or adjacent to the perimeters of the interior components 42 of the filter assembly 10, 10a to prevent the biological fluid from "shortcutting" the interior components 42 (i.e., passing from the inlet port 18 to the outlet port 20, 28 without passing through all of the interior components 42 of the filter assembly 10, 10*a*.

Prior to forming the seal 40, the layers of a multi-layer interior component of the filter assembly 10, 10*a* (e.g., the layers of a multi-layer filtration medium 30) and/or two or more of the interior components of the filter assembly 10, 10*a* (e.g., the filtration medium 30, the frame 32, the pre-filter 36, and/or the post-filter 38) may be sealed together at or adjacent to their peripheral edges. Thus, the seal 40 may be formed using either a two-step method, wherein a peripheral seal is first formed within or amongst the interior components of the filter assembly 10, 10*a* and then the peripheral seal is joined to the filter housing (and any interior components of the filter assembly not included within the peripheral seal), or by a one-step method in which the filter housing and the interior components 42 of the filter assembly 10, 10*a* are joined together simultaneously.

A second or outer seal 44 may also be provided (FIGS. 1, 4, and 5), spaced outwardly of the first seal 40. If provided, the outer seal 44 may join only the two walls 12 and 14 of the filter housing to each other. Alternatively, the frame 32 may also be included in the outer seal 44, between the walls 12 and 14 of the filter housing. Preferably, the outer seal 44 forms a complete seal around the inner seal 40 to prevent leakage of the biological fluid out of the filter assembly 10, 10*a*.

Similar to the inner seal 40, the outer seal 44 may be formed by the application of pressure and radio-frequency heating to the two walls 12 and 14 of the filter housing or by a different sealing process. The seals 40 and 44 may be formed in sequential sealing processes, which is represented in FIGS. 6A-6C, with FIG. 6B representing a step in which the inner seal 40 is formed and FIG. 6C representing a step in which the outer seal 44 is formed. Alternatively, the inner and outer seals 40 and 44 may be formed simultaneously, in a single sealing process, which can be understood as proceeding directly from an assembling or stacking stage (FIG. 6A) to a dual-sealing stage (FIG. 6C).

If two seals 40 and 44 are provided, there may or may not be an unsealed area 46 between them. If there is an unsealed area 46 between the two seals 40 and 44, the outer perimeter of the filtration medium 30 and the frame 32 (and, if provided, the pre-filter 36 and the post-filter 38) may be positioned therein, as shown in FIGS. 4 and 5. By such a configuration, the unsealed area 46 provides the filter assembly 10, 10*a* with a softened or cushioned periphery. If provided, the cushioned periphery provides enhanced protection against damage to tubing and bags of the associated fluid processing set if the bags, tubing, and filter assembly 10, 10*a* of the set are centrifuged.

Figure 7B:
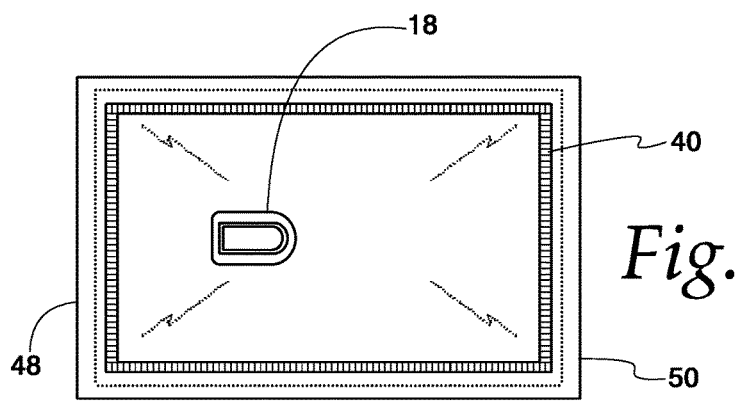
Figure 7C:
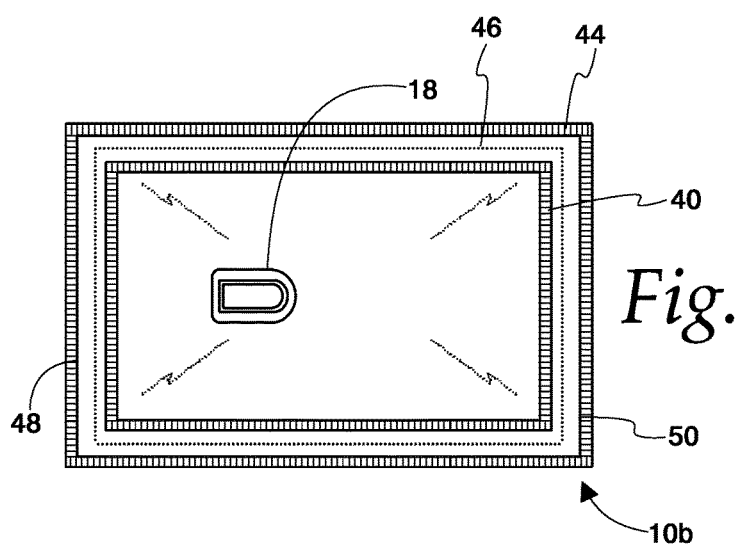

As described above, the filter housing may be formed of a pair of flexible sheets (FIGS. 6A-6C) or a single sheet of tubular material 16 (FIGS. 7A-7C) or a single sheet of material that is folded in half onto itself, with only minor variations between the manufacturing methods thereof. For example, if the filter housing is formed using two sheets of material, the interior components of the filter assembly are positioned therebetween prior to forming the seals. In contrast, if the filter housing is formed using a single sheet of tubular material 16, the interior components 42 of the filter assembly 10*b* may be inserted into an open interior defined by the housing sheet 16 (FIG. 7A) prior to the seals 40 and 44 being formed (FIGS. 7B and 7C). If the filter housing is formed from a single sheet of material that is folded onto itself, the interior components of the filter assembly are positioned between the two portions of the sheet that are folded into facing relationship prior to the seals being formed.

Another manufacturing difference is related to the extent of the outer seal 44 along the edges of the filter housing. In particular, if the filter housing is formed from two sheets of material, it is preferable to form the outer seal 44 along all of the edges of the housing sheets. In contrast, if the filter housing is formed from a single sheet of material, the outer seal 44 need not be formed along all of the edges of the housing. For example, if the filter assembly is formed by inserting the interior components of the filter assembly between folded portions of a single housing sheet, the outer seal may be formed at only the three facing, overlapping edge pairs, without forming the outer seal at the folded edge. Similarly, the outer seal may be formed at only the two opposing edges 48 and 50 (FIGS. 7A-7C), without forming the outer seal over the entire outer perimeter of the filter housing, when the filter housing is formed of a tubular sheet of material 16.

FIG. 8 illustrates a sealing die or electrode 52 provided according to known design. A sealing die 52 of the type shown in FIG. 8 (when used in combination with an opposed or facing sealing die that is not illustrated, but may be a mirror image of the illustrated sealing die 52) may be used to press the layers of the filter assembly together and melt at least certain layers to cause the layers between the sealing dies to become sealed together. When sealing dies 52 of the type shown in FIG. 8 are used to form an inner seal 40, filtration medium 30 positioned between the sealing dies 52 is compressed, but remains positioned between the inlet and outlet sides 12 and 14 of the resulting inner seal 40. If the filtration medium 30 is formed of a generally opaque material, such as PBT, the resulting inner seal 40 will be generally opaque (i.e., not substantially transparent or translucent) as well.

While known sealing dies of the type shown in FIG. 8 may be used to form an inner seal 40, it may be preferred to use a sealing die having a different profile to form the inner seal. For example, FIG. 9 illustrates a sealing die or electrode 54 that may be used (in combination with an opposed or facing sealing die that is not illustrated, but may be a mirror image of the illustrated sealing die 54) to form an inner seal. Compared to the sealing die 52 of FIG. 8, the sealing die 54 may have the same or a similar width (e.g., approximately 5.5 mm), but a different cross-sectional profile. For example, the sealing die 52 of FIG. 8 has a substantially flat or planar contact surface 56 extending between inner and outer corners 58 having a relatively small radius (e.g., approximately 1.5 mm in one embodiment). In contrast, the sealing die 54 of FIG. 9 has a generally semi-circular contact surface 60 with a relatively large radius (e.g., approximately 2.75 mm in one embodiment). In use, sealing dies 52 of the type shown in FIG. 8 are typically brought within approximately 1.4-1.8 mm of each other to form a seal, whereas sealing dies 54 of the type shown in FIG. 9 may be brought closer together (e.g., within approximately 1.0-1.4 mm in one embodiment) to form a seal. The other sealing parameters (e.g., pressure, energy, and temperature) may be substantially the same when using sealing dies of the type shown in FIG. 8 or FIG. 9.

When sealing dies 54 of the type shown in FIG. 9 are used according to the foregoing method to form an inner seal, the resulting inner seal 40*a* (FIG. 11) will have a central section that is at least substantially (but more preferably completely) free of filtration medium 30. While the sealing dies 54 and component filter materials are selected to result in a central section that is substantially free of filtration medium 30 along the entire extent of the inner seal 40a (i.e., along the entire perimeter that the inner seal 40a defines within the filter assembly), eccentricities in individual manufacturing processes may result in trace amounts of filtration medium 30 present along the inner seal 40a. Accordingly, it should be understood that the central section of the inner seal 40a, in practice, may have small amounts of filtration medium 30 present therein, but the central section of the inner seal 40a is preferably at least substantially free of filtration medium 30 along at least a majority of the extent of the inner seal 40a. If the filtration medium 30 is formed of a generally opaque material, while the other layers present in the inner seal 40a are generally transparent, the complete or substantial exclusion of the filtration medium 30 will result in an inner seal 40a having a central section that is generally transparent along at least a majority of the extent of the inner seal 40a, but more preferably along the entire extent of the inner seal 40a. As used herein, the term "central section" refers to a portion of a seal that is positioned between inner and outer peripheral sections of the seal and is not limited to a section that is centered about the midpoint of the seal.

FIGS. 10 and 11 illustrate the formation of an inner seal 40a (FIG. 11) using sealing dies 54 of the type shown in FIG. 9. In FIGS. 10 and 11, the filter assembly includes inlet and outlet housing walls 12 and 14 (which may be formed of a PVC material), with a multiple-layer filtration medium 30 (which may be formed of a PBT material) positioned therebetween. A pre-filter 36 (which may be formed of a PET material) is positioned between the inlet housing wall 12 and the filtration medium 30, while a frame 32 (which may be formed of a PVC material) is positioned between the outlet housing wall 14 and the filtration medium 30. Although not illustrated, the frame 32 preferably includes an associated mesh (as in FIG. 3A), which is positioned inwardly of the inner seal to be formed. While FIGS. 10 and 11 illustrate an inner seal 40a formed in a filter assembly having a pair of housing walls, a filtration medium, a pre-filter, and a post-filter frame, it should be understood that an inner seal which is transparent and/or at least substantially omits a filtration medium may be formed in a filter assembly having fewer layers (e.g., only a pair of housing walls and a filtration medium) or more or different layers.

When sealing dies 54 of the type shown in FIG. 9 are used to form the inner seal 40a, the inlet and outlet housing walls 12 and 14, the filtration medium 30, and the frame 32 tend to melt, while the pre-filter 36 tends to not melt. Thus, applying pressure to the layers of the filter assembly causes the inlet housing wall 12 to melt, with a portion of the molten inlet housing wall 12 invading the voids of the pre-filter 36 to form an intermingled layer 62 within the inner seal 40a. Rather than invading the voids of the pre-filter 36 and entering the intermingled layer 62, the molten filtration medium 64 tends to be pushed aside, out of a central section 66 of the inner seal 40a and into inner and outer peripheral sections 68 and 70 of the inner seal 40a. The space formerly occupied by the filtration medium 30 in the central section 66 of the inner seal 40a is replaced by an aggregate 72 of melted outlet housing wall 14 and frame 32 material. The aggregate 72 may be pressed into the intermingled layer 62 in the central section 66 of the inner seal 40a, thereby meeting molten inlet housing wall 12 within the confines of the pre-filter 36. Although the molten filtration medium 64 is completely or at least substantially excluded from the central section 66 of the inner seal 40a, it may tend to intermingle with the adjacent layers (i.e., the pre-filter 36 and frame 32) and/or the intermingled layer 62 and aggregate 72 to hold the molten filtration medium 64 within place in the peripheral sections 68 and 70 of the inner seal 40a. The intermingled interface between the molten filtration medium 64 and adjacent layers tends to be extremely thin (e.g., on the order of approximately 50-60 micrometers or less, but preferably less than 150 micrometers), but is sufficiently strong to maintain the filtration medium 30 in place within the filter assembly. Outside of the peripheral sections 68 and 70 of the inner seal 40a, the various layers of the filter assembly may remain un-melted, thereby maintaining their independence from the adjacent layers.

With respect to FIG. 11, the dimensions of the various formations within the inner seal 40a will typically vary, depending on the nature of the materials used and the exact sealing method. However, in one exemplary embodiment, the inlet housing wall 12 has a thickness of approximately 90-250 micrometers in the central section 66 of the inner seal 40a, the intermingled layer 62 has a thickness of approximately 170-300 micrometers in the central section 66, and the aggregate 72 has a thickness of approximately 0.84-1.5 mm in the central section 66. The central section 66 itself may have a width of approximately 0.15-8 mm (e.g., approximately 240 micrometers-1.5 mm in one embodiment or approximately 1.0 mm in a preferred embodiment) and a thickness of approximately 0.2-7 mm (e.g., approximately 1.2-2 mm in one embodiment). In the peripheral sections 68 and 70 of the inner seal 40a, the inlet housing wall 12 may having a greater thickness (e.g., approximately 130-350 micrometers), the intermingled layer 62 may have a wider range of thicknesses (e.g., approximately 150-400 micrometers), the aggregate 72 may have a lesser thickness (e.g., approximately 170-650 micrometers) than in the central section 66 of the inner seal 40a. The thickness of the molten filtration medium 64 may vary in the peripheral sections 68 and 70, typically being thinner adjacent to the central section 66 and thicker at the opposite end of the peripheral section 68, 70. For example, in one embodiment, the molten filtration medium 64 may have a maximum thickness of approximately 1.2 mm and taper to at least substantial non-existence in the central section 66 of the inner seal 40a. The width of each peripheral section 68, 70 may be in the range of approximately 0.5-5 mm in an exemplary embodiment or approximately 2.5 mm in a more preferred embodiment. The length of the interface over which the molten filtration medium 64 is intermingled with the adjacent layers may vary, but in one embodiment is approximately 3.5-4.6 mm, as measured along the edges of the molten filtration medium 64 facing the inlet housing wall 12, the outlet housing wall 14, and the central section 66.

The various dimensions of the filter assembly in and around the inner seal 40a may be measured using any suitable method. In one exemplary embodiment, a cut is made perpendicular to the seal 40a (i.e., from an inner portion of a seal to an outer portion of the seal). The cross-section of the seal 40a formed by the cut is then examined using a magnification device, such as an electron scanning microscope or a digital microscope. The optimal level of magnification may vary, depending on the portion of the seal 40a being observed and the dimension to be measured. For example, it may be suitable to use a 10× magnification to observe and measure certain larger dimensions (e.g., the width of the seal 40a), whereas a greater magnification (e.g., 30× or more) may be preferred for measuring smaller dimensions (e.g., the thickness of the intermingled interface between the molten filtration medium 64 and the adjacent layers).

FIG. 11 and the above dimensions assume a generally symmetrical inner seal 40a, formed by a substantially symmetrical sealing die 54, but it is also within the scope of the present disclosure for an inner seal which is generally transparent and/or at least substantially omits filtration medium to be non-symmetrical. For example, FIG. 12 illustrates an alternative embodiment of a sealing die or electrode 74 that may be used to form an inner seal with a central section that is transparent and/or at least substantially omits a filtration medium. The sealing die 74 of FIG. 12 may be understood as a combination of the sealing dies 52 and 54 of FIGS. 8 and 9, with a generally flat or planar contact surface 76 that extends between a first or inner corner 78 and a second or outer corner 80. The second corner 80 is positioned lower than the first corner 78 (when the sealing die 74 is oriented as the upper sealing die of a pair of opposing or facing sealing dies), such that the contact surface 76 of the sealing die 74 is angled or inclined or slanted with respect to horizontal. The first corner 78 may have a relatively small radius (e.g., comparable to the radius of the corners 58 of the sealing die 52 of FIG. 8), while the second corner 80 may have a larger radius (e.g., comparable to the radius of the contact surface 60 of the sealing die 54 of FIG. 9). The sealing die 74 of FIG. 12 (when used in combination with an opposing or facing sealing die that is not illustrated, but may be a mirror image of the illustrated sealing die 74) may be used to form an inner seal. The sealing die 74 of FIG. 12 may be wider (e.g., approximately 50% wider) than the sealing dies 52 and 54 of FIGS. 8 and 9, in which case the resulting inner seal will be wider than a seal formed using one of the sealing dies 52 and 54.

On account of the shape of the sealing die 74 of FIG. 12, the resulting inner seal will have a central section that is positioned in the vicinity of the second corner 80 of the sealing die 74, rather than being centered about a midpoint of the seal. The seal will have one relatively narrow peripheral section (to the right of the central section in the orientation of FIG. 12) that is comparable to one of the peripheral sections 68, 70 of FIG. 11 and a relatively wide peripheral section (to the left of the central section in the orientation of FIG. 12) that is more comparable to a seal formed using sealing dies 52 of the type shown in FIG. 8). The first corner 78 of the sealing die 74 may be referred to as an inner corner because it may be preferred for the sealing die 74 to be oriented such that the first corner 78 is positioned closer to the center of the layers of the filter assembly than the second corner 80 is when the seal is being formed. However, it is also within the scope of the present disclosure for the sealing die 74 to be oriented such that the second corner 80 is positioned closer to the center of the layers of the filter assembly than the first corner 78 is when the seal is formed.

As described above, an inner seal formed according to the present disclosure may have a central section that is generally transparent or more light-transmissive than a seal having filtration medium present therein. According to one manner of assessing the transparency of the central section of an inner seal, the light transmissivity of the central section of the inner seal may be compared to the light transmissivity of an associated outer seal 44 (if provided) using a conventional light detector. For example, in an exemplary test procedure, a Model ILT1400A radiometer/photometer from International Light Technologies of Peabody, Mass. was used to measure the light transmissivity of three filter assemblies, one manufactured according to the methods described herein and the other two manufactured according to conventional design. A light source emitting a red laser having a wavelength of approximately 635 nm was positioned approximately 19 inches away from a photodetector, with the laser focused off center of the photodetector to prevent photodetector saturation. A baseline reading of 852 $kw/cm^2$ was measured with no filter assembly positioned between the light source and the photodetector. Then, a filter assembly was placed onto the photodetector, with the outer seal positioned at the focus of the laser, and a reading was taken to determine the light transmissivity of the outer seal. The filter assembly was then repositioned to place the inner seal at the focus of the laser and a reading was taken to determine the light transmissivity of the inner seal. In the exemplary test procedure, readings were taken at multiple locations along the outer and inner seals, with one reading being taken at each of the upper, lower, left, and right edges of each seal. The same procedure was then repeated for two other filter assemblies.

The outer seal includes only the inlet and outlet housing walls, which are preferably formed of a generally transparent material. In contrast, the central section of the inner seal includes at least the inlet and housing walls, and may also include other layers (e.g., a pre-filter and post-filter), but with no or substantially no filtration medium. On account of typically having more layers and a greater thickness than the outer seal, the central section of the inner seal will typically have a lower light transmissivity than the outer seal, as demonstrated by the results of the exemplary test procedure. For example, the outer seal of a filter assembly manufactured according to the present disclosure was found to transmit approximately 81-84% of the red laser light, whereas the inner seal of the filter assembly was found to transmit approximately 7-33% of the red laser light. Comparing the light transmissivity of each side of the inner seal to the corresponding side of the outer seal, it was found that the inner seal had a light transmissivity of approximately 8-40% of the light transmissivity of the outer seal. For a first conventional biological fluid filter assembly, the light transmissivity of the outer seal was measured to be approximately 73-84%, while the light transmissivity of the inner seal was measured to be approximately 3-4% (i.e., approximately 3-5% of the light transmissivity of the outer seal). For another conventional biological fluid filter assembly, the light transmissivity of the outer seal was measured to be approximately 67-71%, while the light transmissivity of the inner seal was measured to be approximately 2-3% (i.e., approximately 3-4% of the light transmissivity of the outer seal). Thus, based on the exemplary test procedure, it was found that the relative light transmissivity of the inner seal of a filter assembly manufactured according to the present disclosure (i.e., the light transmissivity of the inner seal divided by the light transmissivity of the outer seal) was found to be at least approximately 100% greater than the relative light transmissivity of the inner seal of a conventional filter assembly.

If the relative light transmissivity of the central section of the inner seal (i.e., the light transmissivity of the central section of the inner seal divided by the light transmissivity of the outer seal) is above a particular percentage (e.g., above approximately 8% or above approximately 20% or above approximately 30%), the central section of the inner seal may be considered to be generally transparent, as the term is used herein. The term "generally transparent" as used in connection with the inner seal is intended as a measure of the light transmissivity of the inner seal, meaning that an inner seal that is translucent, but with a light transmissivity that is within a particular percentage of the light transmissivity of an associated outer seal, may be considered to be "generally transparent." Other methods for measuring the transparency of the inner seal may also be employed without departing from the scope of the present disclosure. For example, if the filter assembly does not include an outer seal, then the light transmissivity of the central section of the inner seal may be compared to the light transmissivity of two sheets of material that correspond to the sheets of material used to form the inlet and outlet housing walls of the filter assembly.

While several embodiments of filter assemblies and methods of manufacturing such filter assemblies are described herein, it should be understood that variations may be made to the described and illustrated filter assemblies and methods without departing form the scope of the present disclosure. For example, rather than including only one or two peripheral seals, filter assemblies according to the present disclosure may be provided with more than two peripheral seals. A third peripheral seal, positioned outwardly of the second or outer seal 44, may be perforated or scored or otherwise weakened to define a tear strip or tear seal between a filter assembly and a consecutively manufactured filter assembly. By such a configuration, a plurality of filter assemblies may be manufactured using elongated rolls of material, with adjacent filter assemblies being torn along the third or outermost peripheral seal to separate the filter assemblies.

EXAMPLES

Without limiting any of the foregoing, the subject matter described herein may be found in one or more apparatus or methods. For example, according to a first exemplary configuration, a biological fluid filter assembly includes first and second flexible housing walls. A filtration medium is at least partially positioned between the two housing walls. A seal joins the housing walls and passes through the filtration medium to define a perimeter within the biological fluid filter assembly, but there is substantially no filtration medium present in a central section of the seal along at least a majority of the extent of the perimeter defined by the seal.

A second exemplary configuration of a biological fluid filter assembly includes a configuration in accordance with the preceding exemplary configuration, in which the first and second walls are generally transparent, the filtration medium is generally opaque, and the central section of the seal is generally transparent along at least a majority of the extent of the perimeter defined by the seal.

A third exemplary configuration of a biological fluid filter assembly includes a configuration in accordance with the preceding exemplary configuration, in which the filtration medium is present in generally opaque peripheral sections of the seal.

A fourth exemplary configuration of a biological fluid filter assembly includes a configuration in accordance with any one of exemplary configurations 1-3, in which a pre-filter is at least partially positioned between the filtration medium and the first housing wall, with the seal joining the housing walls and the pre-filter.

A fifth exemplary configuration of a biological fluid filter assembly includes a configuration in accordance with any one of exemplary configurations 1-4, in which a support member is at least partially positioned between the filtration medium and the second housing wall, with the seal joining the housing walls and the support member.

A sixth exemplary configuration of a biological fluid filter assembly includes a configuration in accordance with any one of exemplary configurations 1-5, in which a mesh is at least partially positioned between the filtration medium and the second housing wall.

A seventh exemplary configuration of a biological fluid filter assembly includes a configuration in accordance with the preceding exemplary configuration, in which the mesh is part of a mesh element. The mesh element includes the mesh integrally formed with a frame that surrounds the mesh to define a perimeter of the mesh element. The seal joins the housing walls and the frame.

An eighth exemplary configuration of a biological fluid filter assembly includes first and second flexible housing walls. A filtration medium is at least partially positioned between the two housing walls. A post-filter mesh is at least partially positioned between the filtration medium and the second housing wall. A seal joins the housing walls.

A ninth exemplary configuration of a biological fluid filter assembly includes a configuration in accordance with the preceding exemplary configuration, in which the seal joins the housing walls and the post-filter mesh.

A tenth exemplary configuration of a biological fluid filter assembly includes a configuration in accordance with the eighth exemplary configuration, in which a frame is positioned between the filtration medium and the second housing wall, with the post-filter mesh being integrally formed with the frame.

An eleventh exemplary configuration of a biological fluid filter assembly includes a configuration in accordance with the preceding exemplary configuration, in which the seal joins the housing walls and the frame.

A twelfth exemplary configuration of a biological fluid filter assembly includes a configuration in accordance with the preceding exemplary configuration, in which the frame is comprised of the same material as the second housing wall and the frame and second housing wall are melted together in at least a portion of the seal.

A thirteenth exemplary configuration of a biological fluid filter assembly includes a configuration in accordance with any one of exemplary configurations 8-12, in which a pre-filter is at least partially positioned between the filtration medium and the first housing wall, with the seal joining the housing walls and the pre-filter.

A fourteenth exemplary configuration of a biological fluid filter assembly includes a flexible housing having first and second walls. The first wall includes an inlet port and the second wall includes an outlet port, with the first and second walls being made of a plastic material. A filtration medium for removing at least one substance from a biological fluid is at least partially positioned between the inlet and outlet ports, with a pre-filter at least partially positioned between the inlet port and the filtration medium. A mesh element having a mesh integrally formed with a frame is at least partially positioned between the outlet port and the filtration medium, with the mesh element being made of the plastic material. A seal is formed by integrating a section of the filtration medium at or adjacent to its perimeter, a section of the pre-filter at or adjacent to its perimeter, a section of the frame of the mesh element, and a section of the first and second walls at or adjacent to their perimeter and over their entire perimeter. The seal includes a central section consisting of a layer consisting only of the plastic material of the first wall and having a thickness in the range of approximately 90-100 micrometers, an intermingled layer in which the plastic material of at least the first wall is intermingled with the pre-filter and having a thickness in the range of approximately 170-200 micrometers, and an aggregate in which the plastic material of at least the second wall and the frame are intermingled and having a thickness in the range of approximately 840-900 micrometers.

A fifteenth exemplary configuration of a biological fluid filter assembly includes a configuration in accordance with the preceding exemplary configuration, in which the seal also includes a pair of peripheral sections, with the peripheral sections positioned at opposite sides of the central section. Each peripheral section includes a layer consisting only of the plastic material of the first wall, an intermingled layer in which the plastic material of at least the first wall is intermingled with the pre-filter, an intermingled interface in which molten filtration medium is intermingled with the pre-filter, a layer consisting only of molten filtration medium, a second intermingled interface in which molten filtration medium is intermingled with the frame, a second intermingled layer in which the plastic material of at least the second wall and the frame are intermingled, and a layer consisting only of the plastic material of the second wall. The intermingled interface and the second intermingled interface of the peripheral sections each have a thickness of less than 150 micrometers.

A sixteenth exemplary configuration of a biological fluid filter assembly includes a configuration in accordance with the preceding exemplary configuration, in which the filtration medium transitions from a molten state at an end of each peripheral section adjacent to the central section of the seal to a non-molten state at an opposite end of each peripheral section.

A seventeenth exemplary configuration of a biological fluid filter assembly includes a configuration in accordance with any one of exemplary configurations 14-16, in which the plastic material is polyvinyl chloride.

An eighteenth exemplary configuration of a biological fluid filter assembly includes first and second flexible housing walls. A filtration medium is at least partially positioned between the two housing walls. A post-filter mesh having a normalized air permeability at a pressure difference of 125 Pa in the range of approximately 40 to approximately 800 cm$^2$/s is at least partially positioned between the filtration medium and the second housing wall. A seal joins the housing walls.

A nineteenth exemplary configuration of a biological fluid filter includes a configuration in accordance with the preceding exemplary configuration, in which the post-filter mesh has a normalized air permeability at a pressure difference of 125 Pa of approximately 81.5 cm$^2$/s.

In another aspect of this subject matter, a first exemplary method of manufacturing a biological fluid filter assembly includes providing first and second flexible housing walls. At least a portion of a filtration medium is positioned between the housing walls. A seal that passes through the filtration medium is formed to join the housing walls and define a perimeter within the biological fluid filter assembly, with substantially no filtration medium being present in a central section of the seal along at least a majority of the extent of the perimeter defined by the seal.

A second exemplary method of the present subject matter includes a method in accordance with the preceding exemplary method, in which the housing walls are generally transparent, the filtration medium is generally opaque, and the seal has a generally transparent central section along at least a majority of the extent of the perimeter defined by the seal.

A third exemplary method of the present subject matter includes a method in accordance with the preceding exemplary method, in which the seal has generally opaque peripheral sections in which the filtration medium is present.

A fourth exemplary method of the present subject matter includes a method in accordance with any one of exemplary methods 1-3, in which at least a portion of a pre-filter is positioned between the filtration medium and the first housing wall, with the seal joining the housing walls and the pre-filter.

A fifth exemplary method of the present subject matter includes a method in accordance with any one of exemplary methods 1-4, in which at least a portion of a support member is positioned between the filtration medium and the second housing wall, with the seal joining the housing walls and the support member.

A sixth exemplary method of the present subject matter includes a method in accordance with any one of exemplary methods 1-5, in which at least a portion of a mesh is positioned between the filtration medium and the second housing wall.

A seventh exemplary method of the present subject matter includes a method in accordance with the preceding exemplary method, with the mesh being integrally formed with a support member defining a frame. The seal joins the housing walls and the frame.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A biological fluid filter assembly comprising:
   a flexible housing having first and second walls;
   a filtration medium at least partially positioned between the first and second walls of the housing;
   a substantially planar post-filter mesh at least partially positioned between the filtration medium and the second wall, the post-filter mesh comprising a semi-permeable layer with material present in a grid or web or crossed arrangement defining a plurality of voids without woven or overlapping strands or strips of material and having a normalized air permeability at a pressure difference of 125 Pa in the range of approximately 40 to approximately 800 cm$^2$/s; and
   a seal joining the first and second walls of the housing.

2. The biological fluid filter assembly of claim 1, wherein the post-filter mesh has a normalized air permeability at a pressure difference of 125 Pa of approximately 81.5 cm$^2$/s.

3. The biological fluid filter assembly of claim 1, wherein the seal joins the first and second walls of the housing and the post-filter mesh.

4. The biological fluid filter assembly of claim 1, further comprising a frame positioned between the filtration medium and the second wall, wherein the post-filter mesh is integrally formed with the frame.

5. The biological fluid filter assembly of claim 4, wherein the seal joins the first and second walls of the housing and the frame.

6. The biological fluid filter assembly of claim 5, wherein
   the frame is comprised of the same material as the second wall, and
   the frame and the second wall are melted together in at least a portion of the seal.

7. The biological fluid filter assembly of claim 1, further comprising a pre-filter at least partially positioned between the filtration medium and the first wall of the housing, wherein the seal joins the first and second walls of the housing and the pre-filter.

8. The biological fluid filter assembly of claim 1, wherein the post-filter mesh is formed of a plastic material.

9. The biological fluid filter assembly of claim 1, wherein the post-filter mesh is formed of a polyvinyl chloride material.

10. The biological fluid filter assembly of claim 1, wherein the post-filter mesh has a varying thickness.

11. The biological fluid filter assembly of claim 1, wherein the post-filter mesh has a generally uniform thickness.

12. The biological fluid filter assembly of claim 1, wherein the voids each have a shape selected from the group consisting of rectangular, square, and diamond-shaped.

13. The biological fluid filter assembly of claim 1, wherein at least two of said voids are differently configured.

14. The biological fluid filter assembly of claim 1, wherein the voids each have a height and width in the range of approximately 0.5-20 mm.

15. The biological fluid filter assembly of claim 1, wherein the voids each have a thickness in the range of approximately 0.5-4 mm.

16. The biological fluid filter assembly of claim 1, wherein the voids are arranged in a uniform pattern.

17. The biological fluid filter assembly of claim 1, wherein the voids are arranged in a non-uniform pattern.

18. The biological fluid filter assembly of claim 1, wherein the post-filter mesh is free-floating with respect to the first and second walls, the filtration medium, and the seal.

19. The biological fluid filter assembly of claim 1, wherein the post-filter mesh has a normalized air permeability at a pressure difference of 125 Pa in the range of approximately 50 to approximately 400 $cm^2/s$.

20. The biological fluid filter assembly of claim 1, wherein the post-filter mesh has a normalized air permeability at a pressure difference of 125 Pa in the range of approximately 70 to approximately 150 $cm^2/s$.

21. The biological fluid filter assembly of claim 1, wherein the post-filter mesh has a generally uniform porosity or permeability.

22. The biological fluid filter assembly of claim 1, wherein the post-filter mesh comprises a molded component.

23. The biological fluid filter assembly of claim 1, wherein the post-filter mesh is configured to allow generally uniform flow therethrough.

* * * * *